United States Patent [19]

Cox et al.

[11] Patent Number: 5,670,656
[45] Date of Patent: Sep. 23, 1997

[54] PROCESS FOR PREPARING PYRROLIDINONES

[75] Inventors: John Michael Cox, Wokingham; Kevin James Gillen, Maidenhead; Russell Martin Ellis, Bracknell; Shaheen Khatoon Vohra, Wokingham; Stephen Christopher Smith, Netherthong; Ian Richard Matthews, Wokingham, all of United Kingdom

[73] Assignee: Zeneca Limited, London, England

[21] Appl. No.: 651,181

[22] Filed: May 24, 1996

[30] Foreign Application Priority Data

May 26, 1995 [GB] United Kingdom ............ 9510744

[51] Int. Cl.$^6$ ............................................. C07D 207/28
[52] U.S. Cl. ................... 548/543; 544/242; 546/278.4; 548/204; 548/236; 548/248; 548/264.1; 564/142
[58] Field of Search ............... 548/543, 204, 548/236, 248, 264.1; 544/242; 546/278.4; 564/142

[56] References Cited

FOREIGN PATENT DOCUMENTS 94 13652 6/1994 WIPO.
95 33719 12/1995 WIPO.

OTHER PUBLICATIONS

K. Katayama et al., "Synthesis and Antiiinflammatory Activities of 3–(3, 5–Di–tert–butyl–4–hydroxybenzylidene)pyrrolidin–ones", *J. Med. Chem.*, (1996), 39(9) 1864–71.

Okawara, Tadashi et al. "Convenient Synthesis of Cyclic Carboxamides from α,β,γ,δ and ε-halocarboxamides under Phase transfer Conditions." *Chem. Pharm. Bull.*, (1982), 30(4), 1225–33.

*Primary Examiner*—Jacqueline Haley
*Attorney, Agent, or Firm*—Joseph R. Snyder; Marian T. Thomson

[57] ABSTRACT

A process for the preparation of a compound of general formula II:

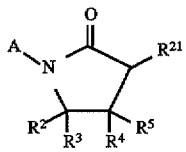

wherein $R^1$ is hydrogen, or $C_1$–$C_{10}$ hydrocarbyl or heterocyclyl having 3 to 8 ring atoms, either of which may optionally be substituted; each $R^2$, $R^3$, $R^4$ and $R^5$ is independently hydrogen or $C_1$–$C_4$ alkyl; A is an optionally substituted aromatic or heteroaromatic ring system; and $R^{21}$ is hydrogen, halogen, OH or OCONHR$^1$, wherein $R^1$ is as defined above; the process comprising cyclizing a compound of general formula III:

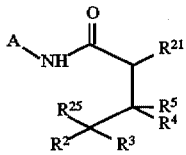

wherein A, $R^2$, $R^3$, $R^4$, $R^5$ and $R^{21}$ are as defined in general formula II and $R^{25}$ is a leaving group such as a halogen atom; under basic conditions.

16 Claims, No Drawings

PROCESS FOR PREPARING PYRROLIDINONES

The present invention relates to a process for the preparation of pyrrolidinone compounds. In particular, the invention relates to the preparation of compounds which are useful as intermediates in the synthesis of agrochemicals such as herbicides.

WO-A-9413652 and UK patent application No 9501158 both describe herbicides and include within their scope compounds of general formula I:

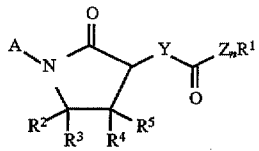

wherein

Z is O, S or $NR^4$;

each $R^4$ and $R^5$ is independently hydrogen or $C_1$–$C_4$ alkyl;

n is 0 or 1;

Y is O, S or $NR^6$;

$R^6$ is H, OH, CHO, $NR^{16}R^{17}$ or $C_1$–$C_{10}$ hydrocarbyl, O-($C_1$–$C_{10}$ hydrocarbyl), either of which may be substituted with up to two substituents chosen from $OR^{16}$, $COR^{16}$, $COOR^{16}$, $OCOR^{16}$, CN, halogen, $S(O)_pR^{16}$ $NR^{16}R^{17}$, $NO_2$, $NR^{16}COR^{17}$, $NR^{16}CONR^{17}R^{18}$, $CONR^{16}R^{17}$ or heterocyclyl;

$R^{16}$, $R^{17}$ and $R^{18}$ are each, independently, hydrogen, $C_1$–$C_6$ hydrocarbyl or $C_1$–$C_6$ halohydrocarbyl;

p is 0, 1 or 2;

alternatively:

when Y is $NR^6$ and either Z is $NR^4$ or n is 0, $R^6$ and the substituents of Z or $R^1$ may together form a bridge represented by the formula —$Q^1$—$Q^2$— or —$Q^1$—$Q^2$—$Q^3$—, where $Q^1$, $Q^2$ and $Q^3$ each independently represent $CR^{12}R^{13}$, =$CR^{12}$, CO, $NR^{14}$, =N, O or S;

each of $R^{12}$ and $R^{13}$ independently represents hydrogen, $C_1$–$C_4$ alkyl, OH or halogen;

$R^{14}$ represents hydrogen or $C_1$–$C_4$ alkyl; $R^1$ is hydrogen or $C_1$–$C_{10}$ hydrocarbyl or heterocyclyl having 3 to 8 ring atoms, either of which may optionally be substituted with halogen (i.e. chlorine, bromine, fluorine or iodine), hydroxy, $SO_2NR^aR^b$ (where $R^a$ and $R^b$ are independently H or $C_1$–$C_6$ alkyl), $SiR_3^c$ (where each $R^c$ is independently $C_1$–$C_4$ alkyl or phenyl), cyano, nitro, amino, mono- and dialkylamino in which the alkyl groups have from 1 to 6 or more carbon atoms, acylamino, $C_1$–$C_6$ alkoxy, $C_1$–$C_6$ haloalkoxy, $C_1$–$C_6$ alkylthio, $C_1$–$C_6$ alkylsulphinyl, $C_1$–$C_6$ alkylsulphonyl, carboxy, carboxyamide, in which the groups attached to the N atom may be hydrogen or optionally substituted lower hydrocarbyl; alkoxy carbonyl wherein the alkoxy group may have from 1 to 6 or more carbon atoms, or aryl such as phenyl; $R^2$ and $R^3$ are each independently hydrogen or $C_1$–$C_4$ alkyl;

A is an aromatic or heteroaromatic ring system optionally substituted with one or more substituents selected from: halogen or $C_1$–$C_{10}$ hydrocarbyl, —O($C_1$–$C_{10}$ hydrocarbyl), —S($C_1$–$C_{10}$ hydrocarbyl), —SO($C_1$–$C_{10}$ hydrocarbyl) or —$SO_2$ ($C_1$–$C_{10}$ hydrocarbyl), cyano, nitro, SCN, $SiR_3^c$ (where each $R^c$ is independently $C_1$–$C_4$ alkyl or phenyl), $COR^7$, $CR^7NOR^8$, NHOH, $ONR^7R^8$, $SF_5$, $COOR^7$, $SO_2NR^7R^8$, $OR^9$ or $NR^{10}R^{11}$; and in which any ring nitrogen atom may be quaternised or oxidised;

alternatively, any two substituents of the group A may combine to form a fused 5- or 6-membered saturated or partially saturated carbocyclic or heterocyclic ring in which any carbon or quaternised nitrogen atom may be substituted with any of the groups mentioned above for A or in which a ring carbon atom may be oxidised;

$R^7$ and $R^8$ are each independently hydrogen or $C_1$–$C_{10}$ hydrocarbyl;

$R^9$ is hydrogen, $C_1$–$C_{10}$ hydrocarbyl, $SO_2(C_1$–$C_{10}$ hydrocarbyl), CHO, CO($C_1$–$C_{10}$ hydrocarbyl), COO ($C_1$–$C_{10}$ hydrocarbyl) or $CONR^7R^8$; $R^{10}$ and $R^{11}$ are each independently hydrogen, $C_1$–$C_{10}$ hydrocarbyl, O($C_1$–$C_{10}$ hydrocarbyl), $SO_2(C_1$–$C_{10}$ hydrocarbyl), CHO, CO($C_1$–$C_{10}$ hydrocarbyl), COO($C_1$–$C_{10}$ hydrocarbyl) or $CONR^7R^8$;

any of the hydrocarbyl groups within the group A may optionally be substituted with halogen (i.e. chlorine, bromine, fluorine or iodine), hydroxy, $SO_2NR^aR^b$ (where $R^a$ and $R^b$ are independently H or $C_1$–$C_6$ alkyl), cyano, nitro, amino, mono- and dialkylamino in which the alkyl groups have from 1 to 6 or more carbon atoms, acylamino, $C_1$–$C_6$ alkoxy, $C_1$–$C_6$ haloalkoxy, $C_1$–$C_6$ alkylthio, $C_1$–$C_6$ alkylsulphinyl, $C_1$–$C_6$ alkylsulphonyl, carboxy, carboxyamide, in which the groups attached to the N atom may be hydrogen or lower hydrocarbyl optionally substituted with halogen; alkoxy carbonyl wherein the alkoxy group may have from 1 to 6 or more carbon atoms, or aryl such as phenyl.

The expression "$C_1$–$C_{10}$ hydrocarbyl" in the foregoing definitions, whether the expression is used on its own or as part of a larger radical such as, for example, $C_1$–$C_{10}$ hydrocarbyloxy, is intended to include hydrocarbyl radicals of up to ten carbon atoms. Subclasses of such hydrocarbyl radicals include radicals with up to four or up to six carbon atoms. The expression "hydrocarbyl" is intended to include within its scope aliphatic, alicyclic, and aromatic hydrocarbyl groups and combinations thereof. It thus includes, for example, alkyl, alkenyl, and alkynyl radicals, cyclopropyl, cyclopropylmethyl, cyclobutyl, cyclopentyl, and cyclohexyl radicals, the adamantyl radical and the phenyl radical. The expression "heterocyclyl" in the foregoing definitions is intended to include both aromatic and non-aromatic radicals. Examples of heteroaromatic radicals include pyridyl, pyrimidyl, triazinyl, thienyl, furyl, oxazolyl, isoxazolyl, and thiazolyl and examples of non-aromatic radicals include partially and fully saturated variants of the above.

The expression "$C_1$–$C_6$ alkyl" refers to fully saturated straight or branched hydrocarbon chains having from one to six carbon atoms. Examples include methyl, ethyl, n-propyl, iso-propyl, t-butyl and n-hexyl. Expressions such as "alkoxy", "cycloalkyl" "alkylthio" "alkylsulphonyl", "alkylsulphinyl" and "haloalkyl" should be construed accordingly.

The expression "$C_2$–$C_6$ alkenyl" refers to a straight or branched hydrocarbon chain having from two to six carbon atoms and at least one carbon-carbon double bond. Examples include ethenyl, 2-propenyl and 2-hexenyl. Expressions such as cycloalkenyl, alkenyloxy and haloalkenyl should be construed accordingly.

The expression "$C_2$–$C_6$ alkynyl" refers to a straight or branched hydrocarbon chain having from two to six carbon atoms and at least one carbon-carbon triple bond. Examples include ethynyl, 2-propynyl and 2-hexynyl. Expressions such as cycloalkynyl, alkynyloxy and haloalkynyl should be construed accordingly.

Subclasses of the above include alkyl, alkenyl or alkynyl groups with up to 4 or up to 2 carbon atoms.

In the context of the present specification the terms "aryl" and "aromatic ring system" refer to ring systems which may be mono-, bi- or tricyclic. Examples of such rings include phenyl, naphthalenyl, anthracenyl or phenanthrenyl. Nitrogen atoms in the ring may be quaternised or oxidised.

In the context of the present specification, the term "heteroaryl" refers to an aromatic ring system containing at least one heteroatom and consisting either of a single ring or of two or more fused rings. Preferably, single rings will contain up to four and bicyclic systems up to five heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, tetrazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, 1,2,3,4-oxatriazolyl, 1,2,3,5-oxatriazolyl, 1,2,3,4-thiadiazolyl, 1,2,3,5-thiadiazolyl, pyridyl, pyrimidinyl, pyridazinyl, pyrazinyl, 1,2,3-triazinyl, 1,2,4-triazinyl, 1,3,5-triazinyl, 1,2,4,5-tetrazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl.

In the context of the present specification, the term "fused saturated or partially saturated carbocyclic or heterocyclic ring system" refers to a fused ring system in which a 5- or 6-membered carbocyclic or heterocyclic ring which is not of aromatic character is fused to an aromatic or heteroaromatic ring system. Examples of such systems include benzimidazolyl, benzoxazolinyl and benzodioxolyl.

WO-A-9413652 teaches various synthetic methods for the preparation of such compounds. For example, compounds of general formula I may be prepared from compounds of the general formula II:

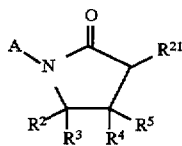

wherein A, $R^2$, $R^3$, $R^4$ and $R^5$ are as defined in general formula I and $R^{21}$ is hydrogen, halogen, OH or $OCONHR^1$, wherein $R^1$ is as defined for general formula I.

Although this method is suitable for the preparation of compounds of general formula I, it is sometimes difficult to prepare the intermediates in sufficiently high yield for the process to be economic. The present inventors have sought to address this problem by providing an improved method for the preparation of herbicidally active pyrrolidone compounds and their intermediates.

In a first aspect of the present invention, there is provided a process for the preparation of a compound of general formula II:

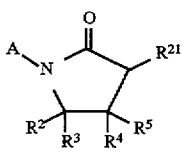

wherein A, $R^2$, $R^3$, $R^4$ and $R^5$ are as defined in general formulae I and $R^{21}$ is hydrogen, halogen, OH or $OCONHR^1$, wherein $R^1$ is as defined for general formula I; the process comprising cyclising a compound of general formula III:

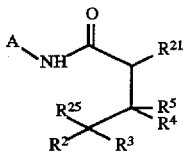

wherein A, $R^2$, $R^3$, $R^4$, $R^5$ and $R^{21}$ are as defined in general formulae I and II and $R^{25}$ is a leaving group such as a halogen atom; under basic conditions.

When $R^{21}$ is $—OCONHR^1$, the compound of general formula II produced in the reaction is a compound of general formula I in which Y is O and Z is N. However, when $R^{21}$ is H, OH or a halogen then further steps are needed to produce a compound of general formula I.

As already mentioned, the cyclisation must be carried out under basic conditions and these may be provided by a strong base such as an alkali metal hydride, alkoxide or hydroxide. Sodium hydride and sodium methoxide or ethoxide have been found to be particularly suitable for this purpose.

The reaction may be carried out in any suitable solvent. The solvent chosen will, however, depend to a large extent upon the base which is used. Thus, when the base is an alkali metal hydride, the solvent may be an organic solvent such as tetrahydrofuran (THF), whilst for an alkoxide, the corresponding alcohol is more appropriate.

Although the group $R^{25}$ may be any leaving group, chloro, bromo and iodo are particularly suitable.

When $R^{21}$ is halogen, a compound of general formula III may be produced from a compound of general formula IV:

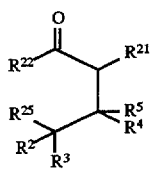

wherein $R^2$, $R^3$, $R^4$, $R^5$ and $R^{25}$ are as defined above and both $R^{21}$ and $R^{22}$ are halogen (though not necessarily the same halogen) by reaction with a compound of general formula V:

wherein A is as defined above for general formula I. The reaction may be conducted in the presence of a base such as triethylamine and in an organic solvent, for example an ether such as diethyl ether or tetrahydrofuran (THF). Usually the reaction temperature will be from about 0° to 100° C., more often about ambient temperature. Compounds of general formula IV are well known or may be prepared by methods such as that described by Ikuta et al in *J. Med. Chem.*, 30, 1995 (1987). Compounds of general formula V are also well known or may be prepared according to known methods by the skilled chemist.

Compounds of general formula III in which $R^{21}$ is OH may be prepared from compounds of general formula VI:

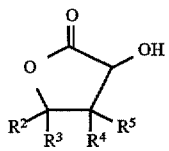

wherein $R^2$, $R^3$, $R^4$ and $R^5$ are as defined above by reaction with a compound of general formula V as defined above. The reaction is carried out in the presence of a reagent such as boron tribromide, aluminium trichloride, tin tetrachloride or titanium tetrachloride and the reaction may take place in an organic solvent such as dichloromethane or dichloroethane. Compounds of general formula VI are readily available or may be prepared by methods known in the art.

A compound of general formula III in which $R^{21}$ is OCONHR$^1$ may be prepared from a compound of general formula III in which $R^{21}$ is OH by reaction with a compound of general formula VII:

$R^1$—N=C=O    VII wherein $R^1$ is as defined for general formula I. This reaction forms part of a further aspect of the invention and will be discussed in more detail below.

Alternatively, a compound of general formula III in which $R^{21}$ is OCONHR$^1$ may be prepared from a compound of general formula VIII:

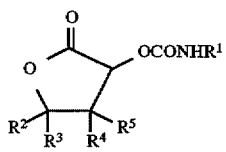

wherein $R^1$, $R^2$, $R^3$, $R^4$ and $R^5$ are as defined above. Firstly, a solution of the compound of general formula VIII in a solvent such as dichloromethane is treated sequentially with trimethylsilyl iodide and oxalyl chloride in a one pot reaction. A compound of general formula V may then be added to the reaction mixture in a solvent such as dichloromethane and in the presence of a base such as pyridine and, optionally, in the presence of 4-N,N-dimethylaminopyridine (DMAP) to give a product of general formula III in which $R^{21}$ is OCONHR$^1$ and $R^{25}$ is I.

A compound of general formula VIII may be prepared from a compound of general formula VI by reaction with a compound of general formula VII as defined above. Again, this reaction forms part of a further aspect of the invention and will be defined in more detail below.

The present inventors have found that, in some circumstances, an alternative method may be used for the preparation of a compound of general formula II in which $R^{21}$ is OH. This is similar to the reaction described above between a compound of general formula VI and a compound of general formula V but different reaction conditions enable a compound of general formula II to be obtained directly.

Therefore in a second aspect of the present invention, there is provided a process for the preparation of a compound of general formula II as defined above and in which $R^{21}$ is OH, the process comprising reacting a compound of general formula V with a compound of general formula VI as defined above and wherein $R^2$ and $R^3$ are preferably hydrogen and $R^4$ and $R^5$ are hydrogen. The reaction may be conducted in the absence of a solvent and at a temperature of from about 100° to 300°, preferably about 150°. This reaction is novel and forms a further aspect of the invention.

The reaction works particularly well for compounds in which A is phenyl or substituted phenyl.

As already mentioned, compounds of general formula II in which $R^{21}$ is OCONHR$^1$ are, in fact, compounds of general formula I. However, compounds of general formula II in which $R^{21}$ is OH or halogen may be converted to compounds of general formula I by any suitable method.

Therefore, in a third aspect of the invention, there is provided a process for the preparation of a compound of general formula I as defined above, the process comprising preparing a compound of formula II according to the first aspect of the invention and, if necessary, converting the compound of general formula II into a compound of general formula I.

Examples of methods for converting compounds of general formula II to compounds of general formula I are described in WO-A-9413652 and UK patent application No 9501158 but any method may be used.

For example, a compound of general formula II in which $R^{21}$ is OH may be converted to a compound of general formula I by reaction with a compound of the general formula VII, IX, X or XI:

  IX

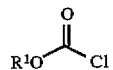  X

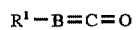  VII

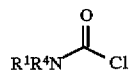  XI wherein $R^1$ is as defined above for general formula I; resulting in the production of compounds of general formula I in which Y is O and in which n is 0, Z is O, Z is NH and Z is NR$^4$ respectively.

Similarly, a compound of general formula II may be reacted with a compound of general formula XII:

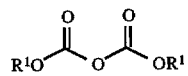  XII wherein $R^1$ is as defined above for general formula I. This gives a compound of general formula I in which Y and Z are both O.

These reactions may be conducted in an organic solvent such as dichloromethane. The reaction with an isocyanate of general formula VII forms part of a further aspect of the invention and will be discussed in more detail below.

Compounds of general formula II in which $R^{21}$ is OH may be converted into compounds of general formula XIII:

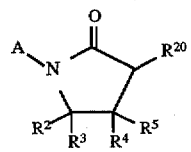  XIII wherein $R^2$ and $R^3$ are as defined for general formula I and $R^{20}$ is bromo, chloro, methane sulfonyloxy or toluene sulfonyloxy. The compounds in which $R^{20}$ is methane or toluene sulfonyloxy may be obtained by reaction with methane sulfonyl chloride or toluene sulfonyl chloride as appropriate although, in some cases, the compound in which $R^{20}$ is chloro may be obtained, particularly in the reaction with methane sulfonyl chloride. The reaction may be conducted at a temperature of from 0° to 30° C., usually at about 5° C., in an organic solvent such as dichloromethane and in the presence of a base such as triethylamine. Compounds of formula XIII wherein $R^{20}$ is chloro may also be prepared by treating compounds of general formula II in which $R^{21}$ is OH with thionyl chloride. The reaction may be conducted in a solvent (e.g. a hydrocarbon, optionally chlorinated) at a moderately elevated temperature (e.g. 50° to 120° C.). Compounds of formula XIII wherein $R^{20}$ is bromo may be prepared by treating compounds of general formula II in which $R^{21}$ is OH with 1,2-dibromotetrachloroethane and triphenyl-phosphine. The reaction may be conducted in a solvent (e.g. an ether) and preferably at ambient temperature (e.g. 15°–30° C.).

Compounds of general formula XIII may be converted into compounds of general formula XIV:

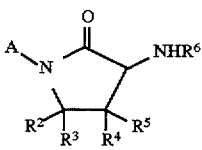

XIV wherein $R^2$, $R^3$ and $R^6$ are as defined for general formula I; by reaction with ammonia or an amine of formula $NH_2R^6$. The reaction may be carried out at a temperature of from 0° to 80° C., preferably from 0° C. to 50° C. It is often the case that the reaction is initiated at 0° C. and subsequently allowed to warm to room temperature after most of the reactant has been converted to product. Usually, the reaction will take place in an organic solvent, particularly an ether such as diethyl ether or tetrahydrofuran (THF).

Compounds of general formula XIV may be converted to compounds of general formula I in which Y is $NR^6$ by reaction with a compound of general formula IX, X, VII or XI using the reaction conditions described above for the conversion of a compound of general formula II to a compound of general formula I.

Compounds of general formula II in which $R^{21}$ is halogen may also be converted to compounds of general formula XIV as defined above and in which $R^6$ is H, by reaction with an alkali metal azide such as sodium azide to give the equivalent azide compound followed by reduction of the azide by any known method, for example using 1,3-propane dithiol in a basic solvent, to give the compound of general formula XIV. The compound of general formula XIV may be converted to a compound of general formula I by the routes described above.

Compounds of general formula II in which $R^{21}$ is halogen, particularly bromine, may be converted to compounds of general formula XV:

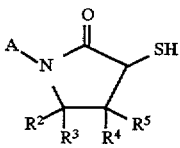

XV by reaction firstly with a thioacid of general formula XVI:

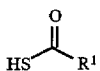

XVI wherein $R^1$ is as defined for general formula I; to give a compound of general formula I in which Y is S and n is 0; followed by reaction with ammonia in a protic solvent such as methanol. The second step may be carried out at a temperature of −10° to 10° C., usually about 0° C. The compound of general formula XV may be converted to a compound of general formula I by reaction with a compound of general formula IX, X, VII or XI as described above for compounds of general formula II in which $R^{21}$ is OH and compounds of general formula XIV.

A compound of general formula II in which $R^{21}$ is hydrogen may be converted to a compound of general formula II in which $R^{21}$ is chlorine or bromine by chlorination or bromination as appropriate. The particular method of halogenation used will depend upon the nature of the group A but, for example, bromination may be carried out by reaction with bromine in the presence of phosphorus tribromide or with N-bromosuccinimide in a halogenated solvent. The reaction will often be conducted at a temperature of from about 70° to 150° C. and in these circumstances it will often be necessary to use a high boiling solvent such as chlorobenzene. An inert atmosphere such as nitrogen may also be employed. The halo derivative of general formula II may then be converted to a compound of general formula I by the route described above.

A compound of general formula II in which $R^{21}$ is hydrogen may be also converted to a compound of general formula II in which $R^{21}$ is OH by reaction with a strong base such as $LiN(Si(CH_3)_3)_2$ or $LiN(CH(CH_3)_2)_2$ followed by reaction with a compound possessing an active oxygen, such as a compound of general formula XVII:

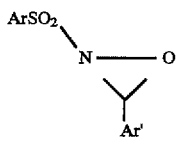

XVII in which, for example, Ar is a p-tolyl group and Ar' is a phenyl group. The reaction is suitably effected in a solvent such as THF at a temperature of from about 100° to 30° C., preferably from about −80° to 0° C. Again, the resulting hydroxy compound of general formula II may be converted to a compound of general formula I by one of the methods described above. Compounds of general formula XVII may be prepared as described in *J. Org. Chem.*, 53, 2087 (1988).

Compounds of general formula I may also be converted to other compounds of general formula I. For example, bridged compounds of general formula I in which Y is $NR^6$ and Z is $NR^4$ and $R^4$ and $R^6$ form a bridge may be synthesised in a variety of ways.

Compounds in which the bridge is represented by the formula —$Q^1$—C(=O)— may be synthesised from compounds of general formula I in which Z is NH and Y is N—$Q^1$—C(=O)—L in which L is a leaving group such as methoxy, ethoxy, chloro and $Q^1$ is as defined above. The reaction is preferably carried out in the presence of a strong base such as sodium hydride, suitably in a solvent such as THF. Usually, the reaction temperature will be in the range of 0° to 80° C., preferably room temperature. They may alternatively be synthesised from compounds of general formula (II) in which $R^{21}$ is a leaving group such as I or Br by reaction with an imidazolinedione of general formula XX

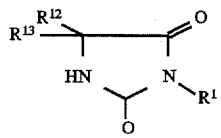

XX where each of $R^{12}$ and $R^{13}$ independently represent hydrogen or $C_1$–$C_4$ alkyl. The reaction is carried out in an organic solvent such as N,N-dimethylformamide or tetrahydrofuran, in the presence of a strong base such as sodium hydride.

Compounds in which the bridge is represented by the formula —C(=O)—C(=O)— or —C(=O)—Q²—C(=O)— may be synthesised from compounds of general formula I in which both Y and Z are NH by reaction with a compound of formula LC(=O)—C(=O)L or LC(=O)—Q²—C(=O)L in which Q² and L are as defined above. The reaction may be carried out in an organic solvent such as toluene at a temperature of from 30° to 120° C. Often, the reaction will be conducted at a temperature of about 80° C.

Compounds in which the bridge is represented by the formula —HC=CH— may be synthesised from compounds of general formula I in which Z is NH and Y is NCH₂CHL₂, wherein L is a leaving group as defined above. The reaction may be carried out in a solvent such as THF under acidic conditions which may be provided by the presence of an aqueous inorganic acid such as hydrochloric acid. The reaction temperature may be from 5° to 50° C. but will, in most cases, be room temperature.

Compounds of general formula I in which the bridge is represented by the formula —CH=CH— may be converted to compounds of general formula I in which the bridge is represented by CH₂—CH₂ by reduction, for example hydrogenation over a palladium or platinum catalyst. Catalytic hydrogenations may be carried out in a solvent such as ethyl acetate. The reaction usually proceeds at an acceptable rate at room temperature and at a pressure of from 1 to 5 bar.

Compounds in which the bridge is represented by the formula —C(=O)CH₂— may be synthesised from compounds of general formula I in which Y and Z are both NH by reaction with CHO—CHO. The reaction may be conducted under acidic conditions which may be provided by the presence of a catalytic amount of, for example, p-toluene sulphonic acid. An example of a suitable reaction solvent is toluene and the reaction is preferably carried out under Dean and Stark conditions at a temperature of from about 80° to 120° C., typically at 110° C. Similar reaction conditions may also be used for the synthesis of compounds of general formula I in which the bridge is represented by the formula —CH₂—OCH₂—. However, in this case, paraformaldehyde is used in place of the CHO—CHO. This particular reaction may be adapted by those skilled in the art for the synthesis of other bridged compounds.

It will be noted that many of the synthetic routes described above involve the reaction of a compound with an isocyanate of general formula VII. WO-A-9413652 describes similar reactions which are carried out in an organic solvent and in the presence of an amine. However, the present inventors have developed an improved method for reacting a substrate with an isocyanate.

Therefore, in a fourth aspect of the invention there is provided a process for the preparation of a compound of one of the following general formulae:

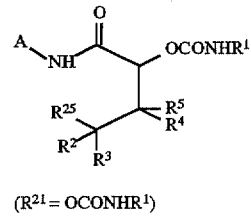

(R²¹ = OCONHR¹)

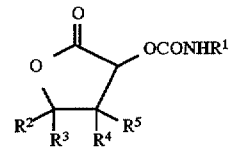

(R²¹ = OCONHR¹)

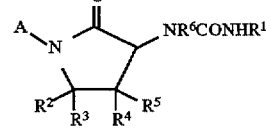

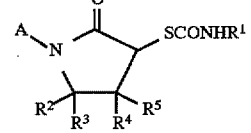

wherein R¹, R², R³, R⁴, R⁵, R⁶ and R²⁵ are as defined above; the process comprising reacting a compound of one of the following general formulae:

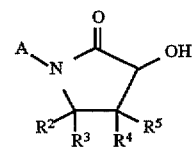

(R²¹ = OH)

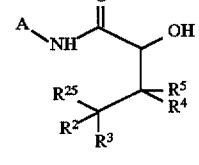

(R²¹ = OH)

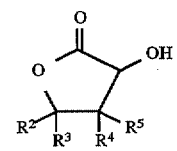

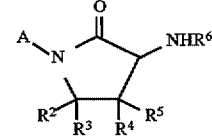

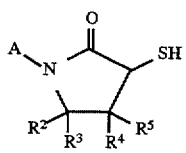

wherein $R^1$, $R^2$, $R^3$, $R^4$, $R^5$, $R^6$ and $R^{25}$ are as defined above; respectively with an isocyanate of general formula VII:

$R^1$—N=C=O  VII wherein $R^1$ is as defined for general formula I in the presence of an acid, especially a Lewis acid, for example boron trifluoride etherate.

Catalytic amounts of Lewis acids may be sufficient to ensure that the reaction proceeds satisfactorily. The use of acids such as boron trifluoride etherate in place of the base used in previous methods may lead to a considerable increase in the yield of the process.

It is preferred that the reaction is carried out in a solvent such as chloroform, dichloromethane or toluene and at a temperature of from about 0° to 50° C., most preferably room temperature.

The invention will now be described in greater detail with reference to the following examples. Compounds 1 to 32 (see Formula (I) to which the examples refer are set out in Table I.

TABLE I

| Compd. No. | A | Y | Z | R1 |
|---|---|---|---|---|
| 1 | 4-trifluoromethyl-pyridin-2-yl | O | NH | C(Me)3 |
| 2 | 2-trifluoromethyl-pyridin-4-yl | O | NH | C(Me)3 |
| 3 | 2-chloropyridin-4-yl | O | NH | C(Me)3 |
| 4 | 4-chloropyridin-2-yl | O | NH | C(Me)3 |
| 5 | 2-iodopyridin-4-yl | O | NH | C(Me)3 |
| 6 | 4,6-bistrifluoro-methylpyridin-2-yl | O | NH | C(Me)3 |
| 7 | 6-chloro-4-trifluoromethyl-pyridin-2-yl | O | NH | C(Me)3 |
| 8 | pyridin-3-yl | O | NH | C(Me)3 |
| 9 | pyridin-3-yl N-oxide | O | NH | C(Me)3 |
| 10 | 4-trifluoromethyl-pyrimidin-2-yl | O | NH | C(Me)3 |
| 11 | pyrimidin-5-yl | O | NH | C(Me)3 |
| 12 | pyrazin-2-yl | O | NH | C(Me)3 |
| 13 | 6-chloropyrimidin-4-yl | O | NH | C(Me)3 |
| 14 | 6-chloro-2-methyl-thiopyrimidin-4-yl | O | NH | C(Me)3 |
| 15 | 6(2,2-difluoroethoxy)-pyrimidin-4-yl | O | NH | C(Me)3 |
| 16 | 6(2,2-trifluoroethoxy)-pyrimidin-4-yl | O | NH | C(me)3 |
| 17 | 6-difluoromethoxy-pyrimidin-4-yl | O | NH | C(Me)3 |
| 18 | 6-difluoromethoxy-2-methoxypyrimidin-4-yl | O | NH | C(Me)3 |
| 19 | 6-trifluoromethyl-pyrimidin-4-yl | O | NH | C(Me)3 |
| 20 | 5-bromothiazol-2-yl | O | NH | C(Me)3 |
| 21 | 5-trifluoromethyl-thiazol-2-yl | O | NH | C(Me)3 |
| 22 | 5-iodothiazol-2-yl | O | NH | C(Me)3 |
| 23 | 5-chlorothiazol-2-yl | O | NH | C(Me)3 |
| 24 | 3-trifluoromethyl-isoxazol-5-yl | O | NH | C(Me)3 |
| 25 | 4-trifluoromethyl-oxazol-2-yl | O | NH | C(Me)3 |
| 26 | 2,2-difluoro-1,3-benzodioxol-5-yl | O | NH | C(Me)3 |
| 27 | 4-trifluoromethyl-pyridin-2-yl | NCH3 | — | C(Me)3 |
| 28 | 4-trifluoromethyl-pyridin-2-yl | NCH3 | — | CH2C(Me)3 |
| 29 | 5-trifluoromethyl-thiazol-2-yl | NCH3 | NH | C(Me)3 |
| 30 | 5-trifluoromethyl-thiazol-2-yl | NCH3 | — | CH2C(Me)3 |
| 31 | 2,2-difluoro-1,3-benzodioxol-5-yl | NCH3 | NH | C(Me)3 |
| 32 | 2,2-difluoro-1,3- | NCH3 | — | CH2C(Me)3 |

TABLE I-continued

| Compd. No. | A | Y | Z | R1 |
|---|---|---|---|---|
|  | benzodioxol-5-yl |  |  |  |
| 33 | 3-trifluoromethylphenyl | O | NH | C(Me)3 |
| 34 | 3-trifluoromethylphenyl | O | — | pyrrol-2-yl |
| 35 | 3-trifluoromethoxyphenyl | O | NH | C(Me)3 |
| 36 | 3-difluoromethoxyphenyl | O | NH | C(Me)3 |
| 37 | 3-chloro-4-fluorophenyl | O | NH | C(Me)3 |
| 38 | 3-difluoromethylphenyl | O | NH | C(Me)3 |

EXAMPLE 1

A general route to 3-hydrocarbyl-carbamoyloxypyrrolidinones exemplified with Compound 1: 3-t-Butylcarbamoyloxy-1(4-trifluoromethyl pyridin-2-yl)pyrrolidin-2-one Step 1 Preparation of 3-t-butylcarbamoyloxy-tetrahydrofuran-2-one Boron trifluoride diethyl etherate (1.38 g) was added dropwise, over a period of fifteen minutes, to a stirred solution of 3-hydroxytetrahydrofuran-2-one (10.0 g) and t-butylisocyanate (9.7 g) in dry dichloromethane (300 ml), whilst maintaining the temperature below 10° C. The mixture was stirred at room temperature for a further four hours, treated with brine and sufficient aqueous sodium bicarbonate solution to render the aqueous phase basic, then extracted several times with dichloromethane. The extracts were washed with brine, dried over magnesium sulphate and evaporated under reduced pressure to give the title compound (18.5 g, m.p. 104°–106° C.). NMR (CDCl$_3$): δ 1.34(9H,s); 2.28(1H,m); 2.73(1H.m); 4.28(1H,dt); 4.46(1H, dt); 4.90(1H,bs); 5.31(1H,t). MS: M$^+$ 201.

The addition can also be catalysed using triethylamine or gaseous hydrogen chloride in place of boron trifluoride. However a rearrangement product can be formed in variable amounts which can necessitate purification of the desired material, for example by chromatography on silica using hexane-ethyl acetate (3:1) as eluant. In subsequent preparations of this compound, and of the corresponding compounds prepared as described in Example 2 to 9 inclusive and 12, it was found that the step of adding chlorotrimethyl silane was not necessary.

These preparations may be carried out exactly as described, but with the omission of the step of adding chlorotrimethylsilane.

Step 2 Preparation of 2-t-butylcarbamoyloxy-4-iodo-N(4-trifluoromethylpyridin-2-yl)butanamide.

A stirred solution of 3-t-butylcarbamoyloxy-tetrahydrofuran-2-one (1.0 g, prepared as described in Step 1 above) in dry dichloromethane (25 ml) was placed under nitrogen and kept dark with an aluminium foil shroud. It was treated dropwise with iodotrimethylsilane (1.0 g), allowed to stand overnight at room temperature, treated with chlorotrimethylsilane (1.09 g) and stirred for a further three hours. It was then cooled to 0° C. and treated dropwise with oxalyl chloride (0.63 g) and N,N-dimethylformamide (0.05 g). After stirring for thirty minutes at 0° C. and a further two hours at 20° C., the mixture was evaporated under reduced pressure. The residue was dissolved in dichloromethane (25 ml) and treated successively, with stirring, with pyridine (2.36 g), 4-dimethylaminopyridine 0.06 g) and 2-amino-4-trifluoromethylpyridine (0.89 g). The mixture was allowed to stand overnight at room temperature, diluted with dichloromethane, washed with hydrochloric acid (2M) and brine, dried over magnesium sulphate and evaporated under reduced pressure. The residue was chromatographed on silica, using dichloromethane-ethanol (99:1) as eluant, to give the title compound (1.11 g, m.p. 83°–85° C.). NMR (CDCl$_3$): δ 1.35(9H,s); 2.5(2H,m); 3.25(2H,t); 5.0(1H,bs); 5.3(1H,dd); 7.3(1H,dd); 7.45(1H,d); 8.55(1H,bs); 8.8(1H, bs). MS: M$^+$ 473.

Step 3 Preparation of 3-t-butylcarbamoyloxy-1(4-trifluoromethylpyridin-2-yl)pyrrolidin-2-one Sodium hydride (0.090 g, 55% suspension in mineral oil) was added portionwise to a stirred solution of 2-t-butylcarbamoyloxy-4-iodo-N(4-trifluoromethylpyridin-2-yl)butanamide (0.97 g, prepared as described in Step 2 above) in dry tetrahydrofuran (10 ml). After stirring for a further fifteen minutes, the mixture was poured on to water and extracted with ethyl acetate. The extracts were washed with brine, dried over magnesium sulphate and evaporated under reduced pressure. The residue was chromatographed on silica, using dichloromethane-ethanol (49:1) as eluant, to give Compound 162 (0.45 g, m.p. 115.5°–116.5° C.). NMR (CDCl$_3$): δ 1.35(9H,s); 2.15(1H,m); 2.7(1H,m); 3.9(1H,m); 4.25(1H,m); 4.9(1H,bs); 5.45(1H,t); 7.3(1H,dd); 8.55(1H, d); 8.75(1H,s). MS: MH$^+$ 346.

EXAMPLE 2

Preparation of Compounds 2 to 7

By procedures similar to those described in Example 1, the appropriate heterocyclic amines were converted into the pyrrolidinone carbamates via the open-chain iodo-amides.

Compound 2

4-Amino-2-trifluoromethylpyridine (1.20 g), scaled to 3-t-butyl-carbamoyloxy-tetrahydrofuran-2-one (1.50 g) and corresponding quantifies of other reagents/solvents, gave 2-t-butylcarbamoyloxy-4-iodo-N(2-trifluoromethylpyridin-4-yl)butanamide (1.15 g, contaminated with starting lactone). NMR (CDCl$_3$) for product only: δ 1.39(9H,s); 2.41(2H,m); 3.26(2H,m); 5.03(1H,bs); 5.21(1H,m); 7.67 (1H,dd); 7.83(1H,d); 8.58(1H,d); 8.93(1H,bs). Cyclisation of this crude material with sodium hydride in tetrahydrofuran gave Compound 2 (0.20 g, m.p. 101°–104° C.). NMR (CDCl$_3$): δ 1.35(9H,s); 2.20(1H,m); 2.77(1H,m); 3.82(1H, m); 3.93(1H,dt); 4.90(1H,s); 5.40(1H,t); 7.86(1H,dd); 8.03 (1H,d); 8.69(1H,d). MS: M$^+$ 345.

Compound 3

4-Amino-2-chloropyridine (0.32 g), scaled to 3-t-butylcarbamoyloxy-tetrahydrofuran-2-one (0.50 g) etc., gave 2-t-butylcarbamoyloxy-4-iodo-N(2-chloropyridin-4-yl)butanamide (0.65 g, m.p. 65°–67° C). NMR (CDCl$_3$): δ 1.35(9H,s); 2.4(2H,m); 3.25(2H,m); 5.05(1H,bs); 5.2(1H,t); 7.3(1H,dd); 7.55(1H,d); 8.2(1H,d); 8.9(1H,bs). MS: MH$^+$ 440, 442. Base catalysed cyclisation of this material (0.58 g) gave Compound 3 (0.18 g, m.p. 152°–154° C.). NMR (CDCl$_3$): δ 1.35(9H,s); 2.15(1H,m); 2.75(1H,m); 3.75(2H, m); 4.9(1H,bs); 5.4(1H,t); 7.65(2H,m); 8.35(1H,m). MS: MH$^+$ 312, 314.

Compound 4

2-Amino-4-chloropyridine (0.40 g), scaled to lactonecarbamate (0.63 g) etc., gave 2-t-butylcarbamoyloxy-4-iodo-N (4-chloropyridin-2-yl)butanamide (0.215 g, m.p. 39°–42° C.). NMR (CDCl$_3$): δ 1.35(9H,s); 2.47(2H,m); 3.22(2H,t); 4.98(1H,bs); 5.24(1H,dd); 7.10(1H,dd); 8.18(1H,d); 8.32 (1H,d); 8.62(1H,bs). MS: M$^+$ 439, 441. Base-catalysed cyclisation of this material (0.17 g) gave Compound 4 (0.055 g, m.p. 133°–135° C.). NMR (CDCl$_3$): δ 1.37 (9H,s); 2.09(1H,m); 2.68(1H,m); 3.85(1H,m); 4.23(1H,dt); 4.90 (1H,bs) 5.42(1H,t); 7.09(1H,dd); 8.26(1H,d); 8.52(1H,d). MS: M$^+$ 311, 313.

Compound 5

4-Amino-2-iodopyridine (0.90 g), scaled to lactonecarbamate (1.0 g) etc., gave the corresponding iodo-amide (0.26 g, m.p. 76°–77° C.). NMR (CDCl$_3$): δ 1.3(9H,s); 2.35(2H,m); 3.25(2H,m); 5.15(1H,t); 5.2(1H,bs); 7.4(1H, dd); 7.8(1H,d); 8.15(1H,d); 9.15(1H,bs). MS: MH$^+$ 532. Base-catalysed cyclisation of this material (0.22 g) gave Compound 5 (0.14 g, m.p. 69°–70° C.). NMR (CDCl$_3$): δ 1.35(9H,s); 2.15(1H,m); 2.7(1H,m); 3.8(2H,m); 5.0(1H,bs); 5.35(1H,t); 7.7(1H,dd); 8.0(1H,d); 8.3(1H,d). MS: MH$^+$ 404.

Compound 6

2-Amino-4,6-bistrifluoromethylpyridine (1.72 g), scaled to lactonecarbamate (1.50 g) etc, gave the corresponding iodo-amide (0.94 g, m.p. 127°–131° C.). NMR (CDCl$_3$): δ 1.39(9H,s); 2.46(2H,m); 3.24(2H,t); 5.03(1H,bs); 5.26(1H, dd); 7.64(1H,d); 8.74(1H,d); 8.86(1H,bs). MS: M$^+$ 541. Base-catalysed cyclisation of this material (0.15 g) gave Compound 6 (0.098 g, m.p. 123°–126° C.). NMR (CDCl$_3$): δ 1.37(9H,s); 2.15(1H,m); 2.72(1H,m); 3.92(1H,m); 4.33 (1H,dt); 4.90(1H,bs); 5.48(1H,t); 7.63(1H,s); 8.99(1H,s). MS: MH$^+$ 414.

Compound 7

2-Amino-6-chloro-4-trifluoromethylpyridine (1.08 g), scaled to lactonecarbamate (1.0 g) etc., gave the corresponding iodo-amide (1.14 g, m.p. 115°–116° C.). NMR (CDCl$_3$): δ 1.35(9H,s); 2.5(2H,m); 3.2(2H,t); 5.0(1H,bs); 5.25(1H, dd); 7.35(1H,s); 8.45(1H,s); 8.7(1H,bs). MS: MH$^+$ 508, 510. Base-catalysed cyclisation of this material (0.50 g) gave Compound 7 (0.21 g, m.p. 149°–151° C.). NMR (CDCl$_3$): δ 1.35(9H,s); 2.1(1H,m); 2.7(1H,m); 3.85(1H,m); 4.25(1H, m); 4.9(1H,bs); 5.45(1H,t); 7.3(1H,s); 8.7(1H,s). MS: MH$^+$ 379, 381.

EXAMPLE 3

Preparation of Compound 8: 3-t-Butylcarbamoyloxy-1(pyridin-3-yl) pyrrolidin-2-one By a procedure similar to that described in Example 1, 3-aminopyridine (0.47 g), scaled to 3-t-butylcarbamoyloxytetrahydrofuran-2-one (1.0 g) etc., gave a crude product (3.1 g) containing approximately 20 mole % of 2-t-butylcarbamoyloxy-4-iodo-N(pyridin-3-yl) butanamide. The desired product was apparently unstable in the mixture and to chromatography on silica. NMR (CDCl$_3$) for product only: δ 1.38(9H,s); 2.46(2H,m); 3.25(2H,t); 5.12(1H,bs); 5.25(1H,dd); 7.29(1H,m); 8.17(1H,dd); 8.36 (1H,dd); 8.58(1H,d). Base-catalysed cyclisation of this crude material gave Compound 8 (0.18 g, m.p. 129°–131° C.) after several chromatographic separations on silica using dichloromethane-ethanol (19:1) as eluant. NMR (CDCl$_3$): δ 1.35(9H,s); 2.12(1H,m); 2.77(1H,m); 3.86(2H,m); 4.90(1H, bs); 5.36(1H,t); 7.33(1H,dd); 8.28(1H,m); 8.44(1H,dd); 8.76 (1H,d). MS: M$^+$ 277.

EXAMPLE 21

Preparation of Compound 9: 3-t-Butylcarbamoyloxy-1(pyridin-3-yl) pyrrolidin-2-one N-oxide A stirred solution of the pyridine (0.090 g, prepared as described in Example 64) in dichloromethane (10 ml) was treated with m-chloroperbenzoic acid (0.12 g, 55%). After being allowed to stand overnight at room temperature, the mixture was diluted with dichloromethane, washed with aqueous sodium bicarbonate solution and brine, dried over magnesium sulphate and evaporated under reduced pressure.

The residue was chromatographed on silica, using dichloromethane-ethanol (19:1) as eluant, to give Compound 9 (0.070 g, m.p. 224°–225° C.). NMR (CDCl$_3$): δ 1.35(9H,s); 2.17(1H,m); 2.75(1H,m); 3.72(2H,m); 4.92(1H, bs); 5.34(1H,t); 7.27(1H,dd); 7.85(1H,d); 8.05(1H,dd); 8.63 (1H,t). MS: M$^+$ 293.

EXAMPLE 5

Preparation of Compounds 10–19

By procedures similar to those described in Example 1, the appropriate heterocyclic amines were converted into the pyrrolidinone carbamates via the open-chain iodo-amides.

Compound 10

2-Amino-4-trifluoromethylpyrimidine (0.41 g), scaled to lactonecarbamate (0.50 g) etc., gave the corresponding iodoamide, (0.16 g, contaminated with starting lactonecarbamate). NMR (CDCl$_3$) for product only: δ 1.3 (9H,s); 2.3(2H,m); 3.3(2H,t); 4.9(1H,bs); 5.3(1H,t); 7.4(1H, d); 8.95(1H,d); 8.8(1H,bs). Base-catalysed cyclisation of this material gave Compound 10 (0.018 g, m.p. 100°–101° C.). NMR (CDCl$_3$): δ 1.35(9H,s); 2.1(1H,m); 2.7(1H,m); 3.9(1H,m); 4.3(1H,m); 4.9(1H,bs); 5.4(1H,t); 7.4(1H,d); 9.0 (1H,d). MS: MH$^+$ 347.

Compound 11

5-Aminopyrimidine (0.52 g), scaled to lactonecarbamate (1.0 g) etc., gave the corresponding iodo-amide (0.38 g, m.p. 77°–79° C.). NMR (CDCl$_3$): δ 1.35(9H,s); 2.4(2H,m); 3.25 (2H,m); 5.05(1H,bs); 5.25(1H,dd); 8.65(1H,bs); 9.0(3H,s). MS: MH$^+$ 407. Base catalysed cyclisation of this material (0.34 g) gave Compound 11 (0.17 g, m.p. 171°–173° C.). NMR (CDCl$_3$): δ 1.35(9H,s); 2.2(1H,m); 2.8(1H,m); 3.85 (2H,m); 5.0(1H,bs); 5.4(1H,t); 9.05(1H,s); 9.15(2H,s). MS: MH$^+$ 279.

Compound 12

2-Aminopyrazine (0.71 g), scaled to lactonecarbamate (1.50 g) etc., gave the corresponding iodo-, (0.26 g) gave Compound 12 (0.11 g, m.p. 146°–149° C.). NMR (CDCl$_3$): δ 1.36(9H,s); 2.14(1H,m); 2.74(1H,m); 3.84(1H,m); 4.18 (1H,dt); 4.92(1H,s); 5.45(1H,t); 8.35(2H,m); 9.76(1H,d). MS: M$^+$ 278.

Compound 13

4-Amino-6-chloropyrimidine (0.71 g), scaled to lactonecarbamate (1.0 g) etc., gave the corresponding iodo-amide (0.65 g, m.p. 175°–176° C.). NMR (CDCl$_3$): δ 1.35(9H,s); 2.45(2H,m); 3.2(2H,t); 5.0(1H,bs); 5.25(1H,dd); 8.25(1H,s); 8.65(1H,s); 8.8(1H,bs). MS: MH$^+$ 441, 443. Base-catalysed cyclisation of this material (0.54 g) gave Compound 12 (0.16 g, m.p. 117° C.). NMR (CDCl$_3$): δ 1.35(1.35(9H,s); 2.15(1H,m); 2.7(1H,m); 3.8(1H,m); 4.25(1H,m); 4.9(1H,s); 5.4(1H,t); 8.5(1H,d); 8.75(1H,s). MS: M$^+$ 312, 314.

Compound 14

4-Amino-6-chloro-2-methylthiopyrimidine (1.02 g), scaled to lactonecarbamate (1.0 g) etc., gave the corresponding iodo-amide (1.08 g, m.p. 131°–132° C.). NMR (CDCl$_3$): δ 1.35(9H,s); 2.3(2H,m); 2.55(3H,s); 3.2(2H,t); 5.0(1H,bs); 5.2(1H,dd); 7.9(1H,s); 8.7(1H,bs). MS: MH$^+$ 486, 488. Base-catalysed cyclisation of this material (0.88 g) gave Compound 14 (0.065 g, m.p. 165°–167° C.). NMR (CDCl$_3$): δ 1.35(9H,s); 2.1(1H,m); 2.55(3H,s); 2.65(1H,m); 3.8(1H, m); 4.25(1H,m); 4.9(1H,bs); 5.4(1H,t); 8.1(1H,s). MH$^+$ 359, 361.

Compound 15

4-Amino-6(2,2-difluoroethoxy)pyrimidine (0.86 g, m.p. 127° C.) was made by treating 4-amino-6-chloropyrimidine (2.50 g) with sodium 2,2-difluoroethoxide in tetrahydrofuran. Reaction of it (0.91 g), scaled to lactonecarbamate (1.0 g) etc., gave the corresponding iodo-amide (1.28 g, m.p. 42°–44° C.). NMR (CDCl$_3$): δ 1.35(9H,s); 2.5(2H,m); 3.2 (2H,t); 4.6(2H,dt); 5.0(1H,bs); 5.2(1H,dd); 6.1(1H,tt); 7.65 (1H,s); 8.5(1H,s); 8.7(1H,bs). MS: MH$^+$ 487. Base-catalysed cyclisation of this material (1.09 g) gave Compound 15 (0.43 g, m.p. 49°–51° C.). NMR (CDCl$_3$): δ 1.3(9H,s); 2.1(1H,m); 2.7(1H,m); 3.8(1H,m); 4.25(1H,m); 4.6(2H,dt); 4.9(1H,bs); 5.4(1H,t); 6.1(1H,tt); 7.9(1H,s); 8.6 (1H,s). MS: MH$^+$ 359.

Compound 16

4-Amino-6(2,2,2-trifluoroethoxy)pyrimidine (0.61 g, m.p. 113° C.) was made by treating 4-amino-6-chloropyrimidine (1.0 g) with sodium 2,2,2-trifluoroethoxide in N,N-dimethylformamide. Reaction of it (0.59 g), scaled to lactonecarbamate (0.58 g) etc., gave the corresponding iodo-amide (0.55 g, m.p. 46°–47° C.). NMR (CDCl$_3$): δ 1.4(9H,s); 2.5(2H,m); 3.2(2H,t); 4.8(2H,m); 4.95(1H,bs); 5.25(1H,dd); 7.7(1H,s); 8.5(1H,s); 8.65(1H, bs). MS: MH$^+$ 504. Base-catalysed cyclisation of this material (0.44 g) gave Compound 16 (0.21, m.p. 100°–101° C.). NMR (CDCl$_3$): δ 1.3(9H,s); 2.1(1H,m); 2.7(1H,m); 3.8(1H, m); 4.25(1H,m); 4.8(2H,q); 4.9(1H,bs); 5.4(1H,t); 7.9(1H, s); 8.6(1H,s). MS: MH$^+$ 377.

Compound 17

4-Amino-6-difluoromethoxypyrimidine (0.17 g, m.p. 152°–154° C.) was made by passing chlorodifluoromethane into a solution of 4-amino-6-hydroxypyrimidine (0.5 g) in aqueous dioxan at 70° C., in the presence of sodium hydroxide. Reaction of it (0.94 g), scaled to lactonecarbamate (1.06 g) etc., gave the corresponding iodo-amide (1.01 g, pale yellow gum). NMR (CDCl$_3$): δ 1.4(9H,s); 2.5(2H,m); 3.2 (2H,t); 5.0(1H,bs); 5.25(1H,dd); 7.48(1H,t); 7.75(1H,s); 8.5 (1H,s); 8.75(1H,bs). MS: MH$^+$ 473. Base-catalysed cyclisation of this material (0.80 g) gave Compound 17 (0.23 g, m.p. 140°–141° C.). NMR (CDCl$_3$): δ 1.3(9H,s); 2.1(1H,m); 2.7(1H,m); 3.8(1H,m); 4.3(1H,m); 4.9(1H,bs); 5.4(1H,t); 7.5(1H,t); 8.0(1H,s); 9.6(1H,s). MS: MH$^+$ 345.

Compound 18

4-Amino-6-difluoromethoxy-2-methoxypyrimidine (1.73 g, m.p. 112°–113° C.) was made by passing chlorodifluoromethane into a solution of 4-amino-6-hydroxy-2-methoxypyrimidine (4.0 g) in aqueous dioxan at 70° C., in the presence of sodium hydroxide. Reaction of it (0.84 g), scaled to lactonecarbamate (0.80 g) etc., gave the corresponding iodo-amide (0.33 g, m.p. 54°–55° C.). NMR (CDCl$_3$): δ 1.35(9H,s); 2.4(2H,m); 3.2(2H,t); 3.95(3H,s); 4.95(1H,bs); 5.2(1H,dd); 7.4(1H,s); 7.45(1H,t); 8.6(1H,s). MS: M$^+$ 502. Base-catalysed cyclisation of this material (0.29 g) gave Compound 18 (0.12 g, m.p. 107°–108° C.). NMR (CDCl$_3$): δ 1.35(9H,s); 2.1(1H,m); 2.7(1H,m); 3.8 (1H,m); 4.0(3H,s); 4.25(1H,m); 4.95(1H,bs); 5.4(1H,t); 7.45 (1H,t); 7.6(1H,s). MS: MH$^+$ 375.

Compound 19

4-Amino-6-trifluoromethylpyrimidine (1.06 g), scaled to lactonecarbamate (1.0 g) etc., gave the corresponding iodoamide (0.76 g, m.p. 169°–171° C.). NMR (DMSO-d$_6$): δ 1.3(9H,s); 2.4(2H,m); 3.3(2H,t); 5.15(1H,dd); 6.1(1H,bs); 8.55(1H,s); 9.0(1H,s); 10.9(1H,bs). MS: MH$^+$ 475. Base-catalysed cyclisation of this material (0.60 g) gave Compound 19 (0.21 g, m.p. 137° C.).

EXAMPLE 6

Preparation of Compounds 20–26

By procedures similar to those described in Example 1, the appropriate heterocyclic amines were converted into the pyrrolidinone carbamates via the open-chain iodo-amides.

Compound 20

2-Amino-5-bromothiazole (0.45 g), scaled to lactonecarbamate (0.50 g) etc., gave the corresponding iodo-amide (0.45 g, m.p. 59°–61° C.). NMR (CDCl$_3$): δ 1.3(9H,s); 2.5(2H,m); 3.2(2H,t); 4.9(1H,bs); 5.3(1H,dd); 7.4(1H,s); 10.0(1H,vbs). MS: MH$^+$ 490, 492. Base-catalysed cyclisation of this material (0.40 g) gave Compound 20 (0.14 g, m.p. 193°–194° C.). NMR (CDCl$_3$): δ 1.35(9H,s); 2.2(1H, m); 2.8(1H,m); 3.9(1H,m); 4.2(1H,m); 4.9(1H,bs); 5.5(1H, t); 7.4(1H,s). MS: M$^+$ 361, 363.

Compound 21

2-Amino-5-trifluoromethylthiazole (5.57 g of hydrochloride salt after appropriate work-up) was made by treating 2-aminothiazole 5-carboxylic acid (8.20 g) with sulphur tetrafluoride and hydrogen fluoride at 120° C. The anhydrous free base (0.42 g), liberated from the hydrochloride salt with aqueous sodium bicarbonate solution, scaled to lactonecarbamate (0.50 g) etc, gave the corresponding iodo-amide (0.52 g, m.p. 50°–52° C.). NMR (CDCl$_3$): δ 1.3(9H, s); 2.5(2H,m); 3.25(2H,t); 4.95(1H,bs); 5.3(1H,dd); 7.85 (1H,s); 10.6(1H,bs). MS: MH$^+$ 480. Base-catalysed cyclisation of this material (0.45 g) gave Compound 21 (0.13 g, m.p. 189°–190° C.). NMR (CDCl$_3$): δ 1.35(9H,s); 2.25(1H,m); 2.8(1H,m); 4.0(1H,m); 4.3(1H,m); 4.9(1H,bs); 5.5(1H,t); 7.8(1H,m). MS: MH$^+$ 352.

Compound 22

2-Amino-5-iodothiazole (1.30 g, as hydrochloride salt), scaled to lactonecarbamate (1.0 g) etc., gave the corresponding iodo-amide (0.29 g, m.p. 50°–60° C., decomp). NMR (CDCl$_3$): δ 1.32(9H,s); 2.45(2H,m); 3.22(2H,t); 4.85(1H, bs); 5.30(1H,dd); 7.56(1H,s). MS: MH$^+$ 538. Base-catalysed cyclisation of this material (0.22 g) gave Compound 22 (0.14 g, m.p. 199°–201° C.). NMR (CDCl$_3$): δ 1.34(9H,s); 2.20(1H,m); 2.77(1H,m); 3.93(1H,m); 4.24(1H,dt); 4.87 (1H,bs); 5.48(1H,t); 7.53(1H,s). MS: M$^+$ 409.

Compound 23

2-Amino-5-chlorothiazole (0.85 g, as hydrochloride salt), scaled to lactonecarbamate (1.0 g) etc., gave the corresponding iodo-amide (0.50 g, m.p. 119°–122° C.). NMR (CDCl$_3$): δ 1.34(9H,s); 2.46(2H,m); 3.22(2H,t); 4.90(1H,bs); 5.32 (1H,dd); 7.34(1H,s). Base-catalysed cyclisation of this material (0.39 g) gave Compound 23 (0.19 g, m.p. 191°–192° C.). NMR (CDCl$_3$): δ 1.35(9H,s); 2.20(1H,m); 2.77(1H,m); 3.92(1H,m); 4.24(1H,dt); 4.87(1H,bs); 5.48 (1H,t); 7.32(1H,s). MS: M$^+$ 317, 319.

Compound 24

5-Amino-3-trifluoromethylisoxazole (0.76 g), scaled to lactonecarbamate (1.0 g) etc., gave the corresponding iodo-amide (0.91 g, m.p. 100°–102° C.). NMR (CDCl$_3$): δ 1.35 (9H,s); 2.4(2H,m); 3.25(2H,m); 5.05(1H,bs); 5.3(1H,dd); 6.65(1H,s). MS: MH$^+$ 464. Base-catalysed cyclisation of this material (0.79 g) gave Compound 24 (0.19 g, m.p. 181°–182° C.). NMR (CDCl$_3$): δ 1.3(9H,s); 2.2(1H,m); 2.8(1H,m); 3.9(1H,m); 4.15(1H,m); 4.9(1H,bs); 5.4(1H,t); 6.8(1H,s). MS: M+335.

Compound 25

2-Amino-4-trifluoromethyloxazole (0.80 g), scaled to lactonecarbamate (2.0 g) etc., gave the corresponding iodo-amide (0.30 g, brown oil). NMR(CDCl$_3$): δ 1.32(9H,s); 2.40(2H,m); 3.22(2H,m); 5.0(1H,s); 5.27(1H,t); 7.79(1H,s); 9.30(1H,s). MS: M$^+$ 463. Base-catalysed cyclisation of this material (0.20 g) gave Compound 25 (0.095 g, m.p. 150°–151° C.). NMR (CDCl$_3$): δ 1.32 (9H,s); 2.21(1H,m); 2.72(1H,m); 3.90(1H,m); 4.13(1H,m); 4.88(1H,bs); 5.35 (1H,t); 7.83(1H,s).

Compound 26

5-Amino-2,2-difluoro-1,3-benzodioxole (0.79 g), scaled to lactonecarbamate (1.0 g) etc., gave the corresponding iodo-amide (0.53 g, m.p. 135°–135° C.). NMR (CDCl$_3$): δ 1.37(9H,s); 2.43(2H,m); 3.25(2H,t); 4.94(1H,bs); 5.20(1H, dd); 6.99(2H,m); 7.58(1H,dd); 8.32(1H,bs). MS: M$^+$ 484. Base-catalysed cyclisation of this material (0.47 g) gave Compound 26 (0.20 g m.p. 147°–148° C.). NMR (CDCl$_3$): δ 1.34(9H,s); 2.08(1H,m); 2.74(1H,m); 3.80(2H,m); 4.90 (1H,bs); 5.35(1H,t); 7.05(1H,d); 7.14(1H,dd); 7.71(1H,d), MS: M$^+$ 356.

EXAMPLE 7

A general route to 3(N(hydrocarbamoyl) alkylamino)- and 3(N(alkanoyl)alkylamino)- pyrrolidinones exemplified by Compounds 27 and 28 Compound 27: 3(N(t-butylcarbamoyl) methylamino-1(4-trifluoromethyl-pyridin-2-yl) pyrrolidin-2-one Step 1 Preparation of 2,4-dibromo-N(4-trifluoromethylpyridin-2-yl)butanamide.

A solution of 2-amino-4-trifluoromethylpyridine (5.00 g) and triethylamine (3.43 g) in dry tetrahydrofuran (50 ml) was added dropwise, over ten minutes, to a stirred solution of 2,4-dibromobutanoyl chloride (9.51 g) in dry tetrahydrofuran (50 ml), whilst maintaining the temperature below 5° C. The mixture was allowed to stir overnight at room temperature, diluted with hydrochloric acid (1M) and extracted with ethyl acetate. The extracts were washed with brine, dried over magnesium sulphate and evaporated under reduced pressure. The residue was chromatographed on silica, using hexane-ethyl acetate (5:1) as eluant, to give the title compound (10.09 g, yellow gum) sufficiently pure for use in Step 2 below. Rechromatographed material had NMR (CDCl$_3$): δ 2.57(1H,m); 2.74(1H,m); 3.62(2H,m); 4.71(1H, dd); 7.33(1H,dd); 8.49(3H,d+s); 8.84(1H,bs). MS: M$^+$ 388.

Step 2 Preparation of 3-bromo-1(4-trifluoromethylpyridin-2-yl)pyrrolidin-2-one

Sodium hydride (0.82 g, 55–65% dispersion in mineral oil) was added portionwise to a stirred solution of the substrate (7.28 g, prepared as described in Step 1 above) in dry tetrahydrofuran (150 ml). The mixture was stirred for one hour, diluted carefully with water and extracted with ethyl acetate. The extracts were washed with brine, dried over magnesium sulphate, and evaporated under reduced pressure. The residue was chromatographed on silica, using hexane-ethyl acetate (7:1) as eluant, to give the title compound (3.90 g, m.p. 43°–47° C.). NMR (CDCl$_3$): δ 2.48 (1H,m); 2.74(1H,m); 4.21(2H,m); 4.66(1H,dd); 7.32(1H, dd); 8.56(1H,d); 8.74(1H,s). MS: M$^+$ 308,310.

Step 3 Preparation of 3-methylamino-1(4-trifluoromethylpyridin-2-yl)pyrrolidinone Gaseous methylamine was bubbled through a stirred solution of the substrate (2.15 g, prepared as described in Step 2 above) in dry tetrahydrofuran (100 ml) for one hour. The mixture was diluted with water, and extracted with ethyl acetate. The extracts were washed with brine, dried over magnesium sulphate, and evaporated under reduced pressure. The residue was chromatographed on silica, using dichloromethane-ethanol (19:1) as eluant, to give the title compound (1.30 g, m.p. 79°–81° C.). NMR (CDCl$_3$): δ 1.96(1H,m); 2.50(1H,m); 2.56(3H,s); 3.61(1H,dd); 3.86(1H, m); 4.24(1H,m); 7.26(1H,dd); 8.51(1H,d); 8.74(1H,d). MS: M$^+$ 259.

Step 4 Preparation of 3(N(t-butylcarbamoyl)methylamino)-1(4-trifluoromethylpyridin-2-yl)pyrrolidin-2-one A stirred solution of substrate (0.30 g, prepared as described in Step 3 above) in dichloromethane (20 ml) was treated successively with triethylamine (0.12 g) and t-butylisocyanate (0.115 g). The residue was allowed to stir for one hour, diluted with dichloromethane and washed with water and brine. The extracts were dried over magnesium sulphate and evaporated under reduced pressure. The residue was chromatographed on silica, using hexane-ethyl acetate (1:1) as eluant, to give Compound 27 (0.28 g, m.p. 152°–155° C.). NMR (CDCl$_3$): δ 1.38(9H,s); 2.13(1H,m); 2.45(1H,m); 2.85(3H,s); 3.81(1H,m); 4.30(1H,m); 4.44(1H, bs); 5.29(1H,dd); 7.26(1H,dd); 8.53(1H,d); 8.78(1H,s). MS: M$^+$ 358

Compound 28: 3((N(3,3-dimethylbutanoyl))methylamino)-1(4-trifluoromethylpyridin-2-yl)pyrrolidin-2-one A stirred solution of 3-methylamino-1(4-trifluoromethylpyridin-2-yl)pyrrolidin-2-one (0.30 g, prepared as described in Example 7, Step 3, above) in dichloromethane (20 ml) was treated successively with triethylamine (0.13 g) and 3,3-dimethylbutanoyl chloride (0.16 g). After one hour, the mixture was diluted with dichloromethane, washed with water and brine, dried over magnesium sulphate and evaporated under reduced pressure. The residue was chromatographed on silica, using hexane-ethyl acetate (1:1) as eluant, to give Compound 28 (0.31 g, m.p. 47°–53° C.). NMR (CDCl$_3$): δ 1.31(9H,s); 2.31(4H, m+s); 3.09(3H,s); 3.88(1H,m); 4.32(1H,m); 5.22(1H,t); 7.26 (1H,dd); 8.52(1H,d); 8.78(1H,s). MS: M+357.

EXAMPLE 8

Preparation of Compounds 29 and 30

The title compounds were prepared by procedures similar to those described in Example 7 but using 2-amino-5-trifluoromethylthiazole (prepared as described in Example 6) in Step 1. This amine (2.17 g) gave 2,4-dibromo-N(5-trifluoromethylthiazol-2-yl)butanamide (4.50 g, m.p. 113°–115° C.). NMR (CDCl$_3$): δ 2.55(2H,m); 3.65(2H,t); 4.8(1H,dd); 8.0(1H,d). MS: MH$^+$ 395, 397, 399. Base-catalysed cyclisation of this material (4.27 g) gave 3-bromo-1(5-trifluoromethylthiazol-2-yl)pyrrolidin-2-one (2.68 g, m.p. 105°–106° C.). NMR (CDCl$_3$): δ 2.6(1H,m); 2.85(1H, m); 4.25(2H,m); 4.7(1H,dd); 7.8(1H,s). MS: M$^+$ 314, 316. This material (1.0 g) was treated with methylamine in tetrahydrofuran to give 3-methylamino-1(5-trifluoromethylthiazol-2-yl)pyrrolidin-2-one (0.24 g, m.p. 108°–109° C.). NMR (CDCl$_3$): δ 2.1(1H,m); 2.6(4H,m); 3.7(1H,t); 4.0(1H,m); 4.3(1H,m); 7.8(1H,s). MS: M$^+$ 265.

Samples of this amine (0.12 g) were treated with t-butyl isocyanate to give Compound 29 (0.07 g, m.p. 186°–187° C.) and with 3,3-dimethylbutanoyl chloride to give Compound 30 (0.15 g, m.p. 123° C.). Compound 192 had NMR (CDCl$_3$): δ 1.35(9H,s); 2.3(1H,m); 2.6(1H,m); 2.9(3H,s); 3.9(1H,m); 4.35(1H,m); 4.45(1H,bs); 5.1(1H,dd); 7.8(1H, d). MS: M$^+$ 364. Compound 193 had NMR (CDCl$_3$): δ 1.1(9H,s); 2.35(1H,m); 2.6(1H,m); 3.15(3H,s); 4.0(1H,m); 4.35(1H,m); 4.85(1H,bs); 7.8(1H,d). MS: MH$^+$ 364.

EXAMPLE 9

Preparation of Compounds 31 and 32

The title compounds were prepared by procedures similar to these described in Example 7 but using 5-amino-2,2-difluoro-1,3-benzodioxole in Step 1. In this case the intermediate bromopyrrolidine (and chloro contaminant) was converted into the corresponding iodide, by treatment with sodium iodide in acetone, before introduction of the alkylamine functionality. In some cases, higher yields can be obtained.

The aminobenzodioxole (2.00 g) gave the dibromobutanamide (2.46 g). NMR (CDCl$_3$): δ 2.56(1H,m); 2.76(1H, m); 3.63(2H,m); 4.69(1H,dd); 7.04(2H,s); 7.60(1H,t); 8.0 (1H,bs). (This material can be contaminated by varying amounts of the 2-chloro analogue). Base-catalysed cyclisation of this material (2.46 g) gave the 3-bromopyrrolidinone (1.66 g). NMR (CDCl$_3$): δ 2.51(1H,m); 2.76(1H,m); 3.81 (1H,dt); 4.04(1H,m); 4.59(1H,dd); 7.06(1H,d); 7.17(1H,dd); 7.68(1H,d). MS: M$^+$ 319, 321). (This material can be contaminated by varying amounts of the 3-chloro analogue). Treatment of the bromide (1.66 g) with sodium iodide in acetone gave the iodopyrrolidinone (1.82 g, m.p. 71°–74° C.). NMR (CDCl$_3$): δ 2.39(1H,m); 2.62(1H,m); 3.71(1H,dt); 3.92(1H,m); 4.72(1H,dd); 7.05(1H,d); 7.16(1H,dd); 7.67 (1H,d). MS: M$^+$ 367. Further treatment of this material (1.0 g) with gaseous methylamine in tetrahydrofuran gave the 3-methylaminopyrrolidinone (0.74 g, m.p. 65°–69° C.). NMR (CDCl$_3$): δ 1.98(1H,m); 2.49(1H,m); 2.53(3H,s); 2.81 (1H,d); 3.53(1H,dd); 3.77(2H,m); 7.03(1H,d); 7.12(1H,dd); 7.68(1H,d). MS: M$^+$ 270. Samples of this amine (0.20 g) were treated with t-butyl isocyanate to give Compound 31 (0.22 g, m.p. 155°–157° C.) and with 3,3-dimethylbutanoyl chloride to give Compound 32 (0.16 g, m.p. 111°–112° C.). Compound 31 had NMR (CDCl$_3$): δ 1.37(9H,s); 2.13(1H, m); 2.47(1H,m); 2.84(3H,s); 3.75(2H,m); 4.44(1H,bs); 5.17 (1H,dd); 7.04(1H,d); 7.12(1H,dd); 7.73(1H,d). MS: M$^+$ 369. Compound 32 had NMR (CDCl$_3$): δ 1.09(9H,s); 2.20(1H,d); 2.33(2H,d); 2.44(1H,m); 2.88(0.3H,s); 3.07(2.7H,s); 3.80 (2H,m); 5.14(1H,t); 7.03(1H,d); 7.12(1H,dd); 7.71(1H,d). This spectrum is complicated by effects arising from restricted rotation. MS: M+368.

EXAMPLE 10

Preparation of Compound 33: 3-t-Butylcarbamoyloxy-1(3-trifluoromethyl phenyl) pyrrolidin-2-one Step 1a Preparation of 4-chloro-2-hydroxy-N(3-trifluoromethylphenyl)butanamide Titanium tetrachloride (11.0 ml, 1.0M solution of dichloromethane) was added dropwise to a stirred solution of 3-hydroxytetrahydrofuran-2-one (1.0 g) and 3-trifluoromethylanaline (1.58 g) in dry 1,2-dichloroethane (20 ml). After the initial exotherm had subsided, the mixture was heated under reflux for five hours, cooled and stirred vigorously for thirty minutes with an aqueous solution of ethylenediaminetetraacetic acid. It was then extracted several times with dichloromethane. The extracts were washed with hydrochloric acid (2M) and brine, dried over magnesium sulphate and evaporated under reduced pressure. The residue was chromatographed on silica, using dichloromethane-ethanol (49:1) to give the title compound (0.63 g, m.p. 98°–100° C.). NMR (CDCl$_3$): δ 2.2(1H,m); 2.5(1H,m); 3.35(1H,bd); 3.8(2H,m); 4.5(1H,m); 7.4(2H,m); 7.75(1H,d); 7.9(1H,s); 8.7(1H,bs). The corresponding diol (0.08 g) was also obtained as a colourless gum. It too can be conceived of as an intermediate. The use of other Lewis acids gave similar results: aluminium chloride gave chloride-diol (1:4), stannic chloride and titanium tetraisopropoxide gave diol, zinc chloride gave chloride-diol (1:2) and magnesium bromide have bromide-diol (9:1).

Step 1b Preparation of 4-bromo-2-hydroxy-N(3-trifluoromethylphenyl)butanamide.

Boron tribromide (11.0 ml, 1.0M solution in dichloromethane) was added dropwise to a stirred solution of 3-hydroxytetrahydrofuran-2-one (1.0 g) and 3-trifluoromethylphenylaniline (1.58 g) in 1,2- dichloroethane (20 ml). The mixture was stirred overnight at room temperature, poured on to water and extracted with dichloromethane. The extracts were washed with hydrochloric acid (2M) and brine, dried over magnesium sulphate, and evaporated under reduced pressure. The residue was chromatographed on silica, using dichloromethane-ethanol (49:1) as eluant, to give the title compound (0.74 g, m.p. 67°–69° C.). NMR (CDCl$_3$): δ 2.3(1H,m); 2.6(1H,m); 3.5 (1H,bs); 3.6(2H,dd); 4.5(1H,dd); 7.4(2H,m); 7.7 (1H,d); 7.9(1H,s); 8.7(1H,bs). MS: M$^+$ 325, 327.

Step 2: Preparation of 3-hydroxy-1(3-trifluoromethylphenyl)pyrrolidin-2-one.

Sodium hydride (0.016 g, 60% suspension in mineral oil) was added to a stirred solution of the substrate (0.10 g, prepared as described in Step 1a above) in dry tetrahydrofuran (10 ml), whilst maintaining the temperature below 5° C. The mixture was stirred for fifteen minutes, diluted with water and extracted with dichloromethane. The extracts were washed with brine, dried over magnesium sulphate, and evaporated under reduced pressure to give the title compound (0.08 g). NMR (CDCl$_3$): δ 2.1(1H,m); 2.6(1H, m); 3.4(1H,bs); 3.75(2H,m); 4.5(1H,t); 7.4(2H,m); 7.8(2H, m). This material was identical to that prepared by an alternative method in Example 13, Step 1 below. The bromoalcohol, prepared as described in Step 1b above, can be used in similar fashion.

Step 3: Preparation of 3-t-butylcarbamoyloxy-1(3-trifluoromethylphenyl)pyrrolidin-2-one.

This material (now a solid, m.p. 115°–117° C.) was prepared by treatment of the alcohol (0.055 g, prepared as described in Step 2 above) with t-butylisocyanate (0.016 g) and triethylamine (0.021 ml) in dichloromethane, basically as described in WO94/13652, Example 80. The carbamoylation can also be catalysed, in high yield, with boron trifluoride etherate.

EXAMPLE 11

Alternative Procedure for the Preparation of Compound 33: 3-t-butylcarbamoyloxy-1(3-trifluoromethylphenyl)pyrrolidin-2-one Step 1a: Preparation of 2-t-butylcarbamoyloxy-4-chloro-N(3-trifluoromethylphenyl) butanamide.

t-Butylisocyanate (0.093 g) and triethylamine (0.095 g) were added successively to a stirred solution of 4-chloro-2-hydroxy-N(3-trifluoromethylphenyl)butanamide (0.24 g, prepared as described in Example 10, Step 1a above). After a day further aliquots of t-butylisocyanate and triethylamine were added. After a further twenty hours, the mixture was evaporated under reduced pressure and the residue chromatographed under reduced pressure to give the title compound (0.13 g, m.p. 115°–116° C.). NMR (CDCl$_3$): δ 1.4(9H,s); 2.4(2H,m); 3.65(1H,t); 5.0(1H,bs); 5.35(1H,t); 7.35(2H,m); 7.7(1H,d); 7.8(1H,s); 8.6(1H,bs). MS: MH$^+$ 381, 383.

Step 1b: Preparation of 4-bromo-2-t-butylcarbamoyloxy-N (3-trifluoromethylphenyl)butanamide.

By a procedure similar to that described in Step 1a above, 4-bromo-2-hydroxy-N(3-trifluoromethylphenyl)butanamide (0.52 g, prepared as described in Example 10, Step 1b above) was treated with t-butylisocyanate and triethylamine in dichloromethane to give the title compound (0.03 g, m.p. 107°–109° C.). NMR (CDCl$_3$): δ 1.4(9H,s); 2.4(2H,m); 3.6(2H,t); 5.1(1H,bs); 5.3(1H,t); 7.3(2H,m); 7.6(1H,d); 7.8 (1H,bs); 8.8(1H,bs). MS: M$^+$ 424, 426. Under the extended time of this reaction, the major product was that of base-catalysed cyclisation (0.16 g, m.p. 114°–116° C.), identical to material described in Example 10, Step 3 above and Example 11, Step 2 below.

Step 2: Preparation of 3-t-butylcarbamoyloxy-1(3-trifluoromethylphenyl)pyrrolidin-2-one.

Sodium hydride (0.0023 g, 60% dispersion in mineral oil) was added to a stirred solution of the chloro-carbamate (0.020 g, prepared as described in Example 11, Step 1a, above) in tetrahydrofuran (2 ml). After two hours, the mixture was diluted with water and extracted with dichloromethane. The extracts were washed with brine, dried over magnesium sulphate and evaporated under reduced pressure to give the title compound (0.01 g, m.p. 114°–117° C.), identical to material made in Example 10, Step 3 above. Base-catalysed cyclisation of the corresponding bromocarbamate, prepared as described in Example 11, Step 1b, above proceeded similarly.

EXAMPLE 12

Further Alternative Procedure for the Preparation of Compound 33: 3-t-Butylcarbamoyloxy-1(3-trifluoromethylphenyl)pyrrolidin-2-one Step 1: Preparation of 3-t-butylcarbamoyloxytetrahydrofuran-2-one Boron trifluoride diethyl etherate (1.38 g) was added dropwise, over a period of fifteen minutes, to a stirred solution of 3-hydroxytetrahydrofuran-2-one (10.0 g) and t-butylisocyanate (9.7 g) in dry dichloromethane (300 ml), whilst maintaining the temperature below 10° C. The mixture was stirred at room temperature for a further four hours, treated with brine and sufficient aqueous sodium bicarbonate solution to render the aqueous phase basic, then extracted several times with dichloromethane. The extracts were washed with brine, dried over magnesium sulphate and evaporated under reduced pressure to give the title compound (18.5 g, m.p. 104°–106° C.). NMR (CDCl$_3$): δ 1.34(9H,s); 2.28(1H,m); 2.73(1H,m); 4.28(1H,dt); 4.46(1H, dt); 4.90(1H,bs); 5.31(1H,t). MS: M$^+$ 201. The addition can also be catalysed using triethylamine or aqueous hydrogen chloride in place of boron trifluoride. However a rearrangement product can be formed in variable amounts which can necessitate purification of the desired material, for example by chromatography on silica using hexane-ethyl acetate (3:1) as eluant.

Step 2: Preparation of 2-t-butylcarbamoyloxy-4-iodo-N(3-trifluoromethylphenyl)butanamide.

A solution of 3-t-butylcarbamoyloxytetrahydrofuran-2-one (0.61 g, prepared as described in Step 1 above) in dry dichloromethane (30 ml) was placed under nitrogen and kept dark with an aluminium foil shroud. It was treated dropwise with iodotrimethylsilane (0.61 g) and allowed to stir for sixteen hours, treated with chloromethylsilane (0.65 g) and allowed to stir for five hours, cooled to 0° C. and treated with N,N-dimethylformamide (0.03 g), then dropwise with oxalyl chloride (0.38 g). After stirring for one hour at 0° C. and overnight at room temperature, the mixture was evaporated under reduced pressure. The residue was dissolved in dichloromethane (20 ml) and treated successively, with stirring and maintaining the temperature below 5° C., with pyridine (1.44 g) and 3-trifluoromethylaniline (0.98 g). The addition of 4-dimethylaminopyridine, as a catalyst, has been found to be advantageous. The mixture was allowed to stand overnight at room temperature, treated with excess hydrochloric acid (2M) and extracted with dichloromethane. The extracts were washed with brine, dried over magnesium sulphate and evaporated under reduced pressure. The residue was chromatographed on silica, using hexane-ethylacetate (3:1) as eluant, to give the title compound (0.39 g, m.p. 114°–118° C.). NMR (CDCl$_3$): δ 1.38(9H,s); 2.44(2H,m); 3.25(2H,t); 4.94(1H,bs); 5.24(1H,t); 7.37(1H,d); 7.44(1H,t); 7.72(1H, d); 7.82(1H,s); 8.37(1H,bs). MS: MH$^+$ 473.

Step 3: Preparation of 3-t-butylcarbamoyloxy-1(3-trifluoromethylphenyl)pyrrolidin-2-one.

Cyclisation of the iodo-carbamate (prepared as described in Step 2 above) by treatment with sodium hy 10, Step 3.

EXAMPLE 13

Preparation of Compound 34: 3-(2-Pyrrolylcarbonyloxy)-1-(3-trifluoromethyl)phenyl-2-pyrrolidinone Step 1 Preparation of 3-hydroxy-1-(3-trifluoromethyl) phenyl-2-pyrrolidinone (alternative method to that described in Example 10, Steps 1 and 2)

i) 1-(3-trifluoromethyl)phenyl-2-pyrrolidinone-3-carboxylic acid

A suspension of 6,6-dimethyl-5,7-dioxaspiro[2.5]octane-4,8-dione (prepared as described in *Organic Syntheses*, Volume 60, p66–68) (8.00 g) in 3-trifluoromethylaniline (8.05 g) was stirred at room temperature for 24 hours. The mixture was filtered, and the insoluble solid was washed with chloroform. The combined filtrates were washed with 2M hydrochloric acid, brine and then dried (MgSO$_4$). Evaporation of the solvent under reduced pressure left a brown solid, which was recrystallised from chloroform/hexane to give the product as a white, crystalline solid, yield 4.10 g, mp 135°–136° C. (dec).

$^1$H nmr (CDCl$_3$): δ 2.47–2.67 (2H,m), 3.70 (1H,t), 3.92–4.01 (2H,m), 7.00 (broad), 7.45–7.60 (2H,m), 7.81–7.90 (2H,m).

ii) 1-(3-trifluoromethyl)phenyl-2-pyrrolidinone 1-(3-trifluoromethyl)phenyl-2-pyrrolidinone-3-carboxylic acid from (i) (3.60 g) was heated to its melting point, and heating was continued until effervescence ceased (ca 50 minutes). The melt was cooled, dissolved in diethyl ether, and treated with decolourising charcoal. The charcoal was filtered off, and the solvent was removed under reduced pressure to leave a solid residue. This was recrystallised from hexane to give the product as colourless needles, yield 2.20 g, mp 67°–68° C.

$^1$H nmr (CDCl$_3$): δ2.19 (2H,quin), 2.62 (2H,t), 3.89 (2H,t), 7.35–7.53 (2H,m), 7.81–7.93 (2H,m) MS: m/e 229 (M$^+$)

iii) 3-hydroxy-1-(3-trifluoromethyl)phenyl-2-pyrrolidinone

A stirred solution of 1-(3-trifluoromethyl)phenyl-2-pyrrolidinone (prepared as in Steps 1 and 2 of Example 7 above) (1.10 g) in dry tetrahydrofuran (5 ml) was cooled to –70° C. under a nitrogen atmosphere, and a solution of lithium hexamethyldisilazide in hexane (1.0M, 4.9 ml) was added dropwise. The resultant pale yellow suspension was then treated with a solution of N-toluenesulphonyl-3-phenyloxaziridine (prepared as described in *Journal of Organic Chemistry*, (1988), 53, 2087) (2.00 g) in dry tetrahydrofuran (5 ml). The resultant pale yellow solution was allowed to warm to room temperature, and was then quenched with water and acidified to pH5 using 2M hydrochloric acid. The mixture was extracted with diethyl ether (×2), and the combined extracts were washed with water, dried (MgSO$_4$) and evaporated under reduced pressure to leave an oil. Purification by silica gel chromatography, eluting with ethyl acetate/hexane mixtures, afforded the title compound as a clear gum, yield 0.26 g.

$^1$H nmr (CDCl$_3$): δ1.62 (1H,broad s); 2.12(1H,m); 2.63 (1H,m); 3.72–3.90 (2H,m); 4.51(1H,m); 7.39–7.58(2H,m); 7.77–8.02(2H,m). MS: m/e 245 (M$^+$)

Step 1a Further Alternative Preparation of 3-hydroxy-1-(3-trifluoromethyl)phenyl-2-pyrrolidinone α-hydroxy-delta-butyrolactone (2.04 g) and 3-trifluoromethylaniline (2.74 ml) were heated without solvent to 100° C. with stirring. After 4 hours, the temperature was raised to 150° C. (oil bath temperature) and stirring was continued for a further 20 hours. After cooling, the dark red liquid was taken up in dichloromethane (5 ml) and applied to a silica flash column. Elution with ethyl acetate in hexane (a gradient of 40–60% ethyl acetate) gave the title compound as a pale orange crystalline solid (2.42 g).

Physical data identical to that observed for the material prepared in Step 1.

Step 2 Preparation of 2-Pyrrole carboxylic acid chloride.

Oxalyl chloride (0.48 ml) was added to a suspension of 2-pyrrole carboxylic acid (0.45 g) in chloroform (10 ml) at room temperature. After 2 hours, effervescence had ceased and the solvent was evaporated in vacuo to give a solid. Trituration with hexane left the crude crystalline acid chloride which was used directly.

Step 3 Preparation of 3-(2-Pyrrolylcarbonyloxy)-1-(3-trifluoromethyl)phenyl-2-pyrrolidinone.

2-Pyrrole carboxylic acid chloride from Step 2 (0.25 g) was dissolved in dichloromethane (10 ml) along with 3-hydroxy-1-(3-trifluoromethyl)phenyl-2-pyrrolidinone (0.38 g) from Step 1. Triethylamine (0.26 ml) was added. The solution turned reddish-orange and was left stirring overnight at room temperature. After diluting with dichloromethane (100 ml), the solution was washed with sat. NaHCO$_3$ (aq) (2×50 ml), brine (50 ml), dried (Na$_2$SO$_4$) and evaporated. Purification of the residue by flash chromatography on silica, eluting with 30% ethyl acetate in hexane, gave a pale yellow oil which crystallised. Re-crystallisation from ethyl acetate/hexane gave the pure title compound (0.21 g) as colourless crystals, m.p. 127.5°–128° C. $^1$H NMR (CDCl$_3$): δ 2.30(1H,m); 2.81(1H,m); 3.94(2H,m); 5.68(1H,t); 6.30(1H,m); 7.00(1H,m); 7.04(1H,m); 7.45(1H, d); 7.53(1H,t); 7.94(1H,d) overlapping 7.95(1H,s); 9.20(1H, brs).

EXAMPLE 14

Preparation of 3-t-butylcarbamoyloxy-1(2-cyano-5-trifluoromethylphenyl)pyrrolidin-2-one Step 1 Preparation of 2-t-butylcarbamoyloxy-4-iodo-N(2-cyano-5-trifluoromethylphenyl)butanamide.

3-t-Butylcarbamoyloxytetrahydrofuran-2-one (0.1 g) in dichloromethane (4 ml) was screened from light and treated with trimethylsilyl iodide (0.1 g). The mixture was left overnight and then cooled to 0° C. Pyridine (0.236 g) was added, followed by a catalytic amount of 4-dimethyaminopyridine. The mixture was left overnight and then poured into dilute hydrochloric acid. The mixture was extracted with dichloromethane and the extracts washed with brine and dried (magnesium sulphate) and evaporated. The residue was redissolved and passed through a column of silica gel, using a 1:1 mixture of ethyl acetate and hexane as the eluent, to yield the title iodo compound (0.089 g).

Step 2 Preparation of 3-t-butylcarbamoyloxy-1(2-cyano-5-trifluoromethylphenyl)pyrrolidin-2-one.

The product from Step 1 was dissolved in tetrahydrofuran (10 ml) and cooled to 0° C. Sodium hydride (0.008 g of a 55% dispersion in oil) was added, and the mixture allowed to warm to room temperature. The solution was diluted with water and extracted with ethyl acetate. The extracts were dried (magnesium sulphate) and evaporated. The residue was chromatographed on a column of silica gel using a mixture of ethyl acetate and hexane as the eluent. The first compound eluted was 2-cyano-5-trifluoromethylaniline; this was followed by the slower moving title compound (0.025 g)

EXAMPLE 15

Preparation of 1(3-bromo-4-fluorophenyl)3(N(t-butylcarbamoyl)ethylaminopyrrolidin-2-one Step 1: Preparation of 1(3-bromo-4-fluorophenyl)3-hydroxypyrrolidin-2-one.

3-Bromo-4-fluoroaniline (20 g) and 3-hydroxy-2-ketotetrahydrofuran (8.9 g) were mixed and heated to 150° C. for 64 hours. The mixture was allowed to cool and diluted with dichloromethane (200 ml). A solution (37 ml) of sodium hydroxide (10molar) was added and the mixture left to stand for an hour. The solid was filtered off and washed with dichloromethane, and suspended in more dichloromethane (200 ml). The mixture was acidified with concentrated hydrochloric acid and stirred for an hour. The organic layer was separated, washed three times with water, dried (magnesium sulphate) and concentrated to yield a pale brown solid (25.4 g) identified as the title compound. The NMR spectrum was consistent with this structure.

Step 2
Preparation of 1(3-bromo4-fluorophenyl)3-methanesulphonyloxypyrrolidin-2-one.

The pyrrolidin-2-one prepared as described in Step 1 (4.5 g) was dissolved in dichloromethane (50 ml) and cooled to 0° C. Triethylamine (2.8 ml) was added, followed by a solution of methanesulphonyl chloride (1.39 ml) in dichloromethane (15 ml), added dropwise over a period of 30 minutes, while the mixture was maintained at a maximum temperature of 2° C. When addition of the sulphonyl chloride was complete, the mixture was allowed to warm to room temperature and left to stir for 5 hours. It was then left to stand for two days at room temperature, and diluted with dichloromethane. The diluted reaction mixture was then washed three times with water, dried (magnesium sulphate), and concentrated to give a dark brown solid. This was chromatographed on a silica column using a mixture of diethyl ether and hexane (2:1) as the eluent to yield the sulphonyloxy compound as a white powder (6 g). The NMR spectrum was consistent with the expected product.

Step 3
Preparation of 1(3-bromo-4-fluorophenyl)3-ethylaminopyrrolidin-2-one

Sodium iodide (1.1 g), followed by ethylamine (1.92 ml) was added to a solution in tetrahydrofuran (60 ml) of the ethylamino compound prepared in Step 2 (2.6 g). The solution was stirred for two hours and then left to stand overnight. The reaction mixture was then poured into water and extracted with ethyl acetate three times. The extracts were combined, washed twice with water and once with brine, dried (magnesium sulphate), and concentrated to yield a dark brown oil. This was chromatographed on a silica column using a mixture of triethylamine and ethyl acetate (1:9) as the eluent. The title compound was obtained as a yellow solid. The NMR spectrum was consistent with the expected structure.

Step 4
Preparation of 1(3-bromo-4-fluorophenyl)3(N(t-butylcarbamoyl)ethylaminopyrrolidin-2-one t-Butylisocyanate (0.2 ml) was added to a solution of the ethylamino compound prepared in Step 3 (0.31 g) in dichloromethane (8 ml), and the mixture stirred for 90 minutes and then left to stand overnight. The reaction mixture was concentrated, yielding a yellow oil. This was taken up in diethyl ether (3 ml) and hexane added, yielding the title compound as a white solid with a melting point of 118.2° to 119.4° C. The NMR, IR, and mass spectra were consistent with the structure assigned.

EXAMPLE 16

Preparation of 1(3-bromo-4-fluorophenyl)3(3,3-dimethylbutanoylamino)pyrrolidin-2-one Triethylamine (0.28 ml), followed by 3,3-dimethylbutanoyl chloride (0.46 ml) was added to a solution of 1(3-bromo-4-fluorophenyl)3-ethylaminopyrrolidin-2-one, (0.5 g, prepared as in Step 3 of Example 15) in dichloromethane. The mixture was stirred for three hours at room temperature, and then left to stand overnight. It was then poured into water and the mixture extracted with dichloromethane and the extract dried (magnesium sulphate) and evaporated to leave a yellow oil. This was dissolved in diethyl ether and the solution passed through a column of silica using ether as the eluent. Fractions of 25 ml were collected. Fractions 3–8 were combined and evaporated to give the title compound as a clear oil. The NMR, IR, and mass spectra of the product were consistent with the structure assigned.

We claim:

1. A process for the preparation of a compound of formula II:

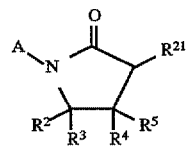

wherein

R$^1$ is hydrogen or C$_1$–C$_{10}$ hydrocarbyl or heterocyclyl having 3 to 8 ring atoms, either of which may optionally be substituted with halogen, hydroxy, SO$_2$NR$^a$R$^b$ where R$^a$ and R$^b$ are independently H or C$_1$–C$_6$ alkyl, SiR$_3{}^c$ where each R$^c$ is independently C$_1$–C$_4$ alkyl or phenyl, cyano, nitro, amino, mono- and dialkylamino, acylamino, C$_1$–C$_6$ alkoxy, C$_1$–C$_6$ haloalkoxy, C$_1$–C$_6$ alkylthio, C$_1$–C$_6$ alkylsulphinyl, C$_1$–C$_6$ alkylsulphonyl, carboxy, carboxyamide in which the groups attached to the N atom may be hydrogen or optionally substituted lower hydrocarbyl, alkoxy carbonyl, or aryl;

each R$^2$, R$^3$, R$^4$ and R$^5$ is independently hydrogen or C$_1$–C$_4$ alkyl;

A is an aromatic or heteroaromatic ring system optionally substituted with one or more substituents selected from: halogen, C$_1$–C$_{10}$ hydrocarbyl, —O(C$_1$–C$_{10}$ hydrocarbyl), —S(C$_1$–C$_{10}$ hydrocarbyl), —SO(C$_1$–C$_{10}$ hydrocarbyl) or —SO$_2$ (C$_1$–C$_{10}$ hydrocarbyl), cyano, nitro, SCN, SiR$_3{}^c$, COR$^7$, CR$^7$NOR$^8$, NHOH, ONR$^7$R$^8$, SF$_5$, COOR$^7$, SO$_2$NR$^7$R$^8$, OR$^9$ and NR$^{10}$R$^{11}$; and in which any ring nitrogen atom may be quaternised or oxidised; or any two substituents of the group A may combine to form a fused 5- or 6-membered saturated or partially saturated carbocyclic or heterocyclic ring in which any carbon or quaternised nitrogen atom may be substituted with any of the substituents mentioned above for A or in which a ring carbon atom may be oxidised;

R$^7$ and R$^8$ are each independently hydrogen or C$_1$–C$_{10}$ hydrocarbyl;

$R^9$ is hydrogen, $C_1-C_{10}$ hydrocarbyl, $SO_2(C_1-C_{10}$ hydrocarbyl), CHO, $CO(C_1-C_{10}$ hydrocarbyl), COO $(C_1-C_{10}$ hydrocarbyl) or $CONR^7R^8$;

$R^{10}$ and $R^{11}$ are each independently hydrogen, $C_1-C_{10}$ hydrocarbyl, $O(C_1-C_{10}$ hydrocarbyl), $SO_2(C_1-C_{10}$ hydrocarbyl), CHO, $CO(C_1-C_{10}$ hydrocarbyl), COO $(C_1-C_{10}$ hydrocarbyl) or $CONR^7R^8$;

any of the hydrocarbyl groups within the group A may optionally be substituted with halogen, hydroxy, $SO_2NR^aR^b$, cyano, nitro, amino, mono- or dialkylamino, acylamino, $C_1-C_6$ alkoxy, $C_1-C_6$ haloalkoxy, $C_1-C_6$ alkylthio, $C_1-C_6$ alkylsulphinyl, $C_1-C_6$ alkylsulphonyl, carboxy, carboxyamide in which the groups attached to the N atom may be hydrogen or lower hydrocarbyl optionally substituted with halogen, alkoxy carbonyl, or aryl;

$R^{21}$ is hydrogen, halogen, OH, or $OCONHR^1$, wherein $R^1$ is as defined above; the process comprising cyclising a compound of formula III:

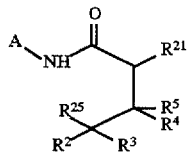

wherein A, $R^2$, $R^3$, $R^4$, $R^5$ and $R^{21}$ are as defined in formula II and $R^{25}$ is a leaving group; under basic conditions.

2. A process as claimed in claim 1, wherein the basic conditions are provided by a strong base.

3. A process as claimed in claim 1, wherein a compound of formula III in which $R^{21}$ is halogen is produced from a compound of formula IV:

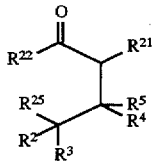

wherein both $R^{21}$ and $R^{22}$ are halogen by reaction with a compound of formula V:

  V in the presence of a base and in an organic solvent.

4. A process as claimed in claim 1, wherein a compound of formula III in which $R^{21}$ is OH is prepared from a compound of formula VI:

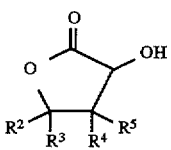

by reaction with a compound of formula V:

  V in the presence of a reagent selected from the group consisting of boron tribromide, aluminium trichloride, tin tetrachloride and titanium tetrachloride and in an organic solvent.

5. A process as claimed in claim 1, wherein a compound of formula III in which $R^{21}$ is $OCONHR^1$ prepared either:

i) from a compound of formula III in which $R^{21}$ is OH by reaction with a compound of formula VII:

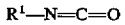  VII wherein $R^1$ is as defined for formula II; or ii) from a compound of formula VIII:

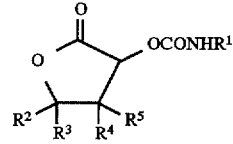

wherein $R^1$, $R^2$, $R^3$, $R^4$ and $R^5$ are as defined above by sequential treatment with trimethylsilyl iodide, and oxalyl chloride in a one pot reaction followed by addition of a compound of formula V:

  V to the reaction mixture in a solvent and in the presence of a base and, optionally, in the presence of dimethylaminopyridine (DMAP).

6. A process as claimed in claim 1, which further comprises the step of converting the compound of formula II into a compound of formula I:

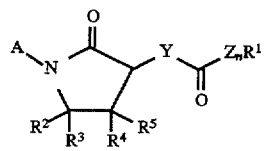

wherein Z is O, S or $NR^4$;

n is 0 or 1;

Y is O, S or $NR^6$;

$R^6$ is H, OH, CHO, $NR^{16}R^{17}$ or $C_1-C_{10}$ hydrocarbyl, —$O(C_1-C_{10}$ hydrocarbyl), either of which may be substituted with up to two substituents chosen from $OR^{16}$, $COR^{16}$, $COOR^{16}$, $OCOR^{16}$, CN, halogen, S(O)$_pR^{16}NR^{16}R^{17}$, $NO_2$, $NR^{16}COR^{17}$, $NR^{16}CONR^{17}R^{18}$, $CONR^{16}R^{17}$ or heterocyclyl;

$R^{16}$, $R^{17}$ and $R^{18}$ are each, independently, hydrogen, $C_1-C_6$ hydrocarbyl or $C_1-C_6$ halohydrocarbyl;

p is 0, 1 or 2; or when Y is $NR^6$ and either Z is $NR^4$ or n is 0, $R^6$ and the substituents of Z or $R^1$ may together form a bridge represented by the formula —$Q^1$—$Q^2$— or —$Q^1$—$Q^2$—$Q^3$—, where $Q^1$, $Q^2$ and $Q^3$ each independently represent $CR^{12}R^{13}$, =$CR^{12}$, CO, $NR^{14}$, =N, O or S;

each of $R^{12}$ and $R^{13}$ independently represents hydrogen, $C_1-C_4$ alkyl, OH or halogen; and $R^{14}$ represents hydrogen or $C_1-C_4$ alkyl.

7. A process as claimed in claim 6, wherein a compound of formula II in which $R^{21}$ is OH is converted to a compound of formula I by reaction with a compound of the formula VII, IX, X, or XI:

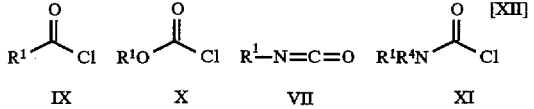

wherein $R^1$ is as defined above for formula II; resulting in the production of compounds of formula I in which Y is O and in which n is 0, Z is O, Z is NH, Z is $NR^4$ and X is O respectively.

8. A process as claimed in claim 6, wherein i) a compound of formula II in which $R^{21}$ is OH is converted into a compound of formula XIII:

XIII wherein $R^{20}$ is bromo, chloro, methane sulfonyloxy or toluene sulfonyloxy, by reaction with a chlorinating agent, a brominating agent, methane sulfonyl chloride or toluene sulfonyl chloride, in the presence of a base;

ii) the compound of formula XIII is converted into a compound of formula XIV:

XIV by reaction with ammonia or an amine of formula $NH_2R^6$; and iii) the compound of formula XIV is converted to a compound of formula I in which Y is $NR^6$ by reaction with a compound of formula IX, X, VII or XI:

IX

X

VII

XI

9. A process as claimed in claim 6, wherein:

ia) a compound of formula II in which $R^{21}$ is halogen is converted to a compound of formula XIV:

XIV by reaction with an alkali metal azide to give the equivalent azide compound followed by reduction of the azide; or ib) a compound of formula II in which $R^{21}$ is halogen, is converted to a compound of formula XV:

XV by reaction firstly with a thioacid of formula XVI:

XVI to give a compound of formula I in which Y is S and n is 0; followed by reaction with ammonia in a protic solvent such as methanol; and ii) the compound of formula XIV or XV produced by step ia or ib is converted to a compound of formula I by reaction with a compound of formula IX, X, VII or XI:

IX

X

VII

XI

10. A process according to claims 1, 5 or 6, wherein a compound of one of the following formulae:

II ($R^{21}$ = $OCONHR^1$)

III ($R^{21}$ = $OCONHR^1$)

VIII

XVIII

XIX wherein;

$R^1$ is hydrogen or $C_1$–$C_{10}$ hydrocarbyl or heterocyclyl having 3 to 8 ring atoms, either of which may optionally be substituted with halogen, hydroxy, $SO_2NR^aR^b$ where $R^a$ and $R^b$ are independently H or $C_1$–$C_6$ alkyl, SiR₃ᶜ where each Rᶜ is independently C₁–C₄ alkyl or phenyl, cyano, nitro, amino, mono- and dialkylamino, acylamino, C₁–C₆ alkoxy, C₁–C₆ haloalkoxy, C₁–C₆ alkylthio, C₁–C₆ alkylsulphinyl, C₁–C₆ alkylsulphonyl, carboxy, carboxyamide in which the groups attached to the N atom may be hydrogen or optionally substituted lower hydrocarbyl, alkoxy carbonyl, or aryl;

each $R^2$, $R^3$, $R^4$ and $R^5$ is independently hydrogen or C₁–C₄ alkyl;

A is an aromatic or heteroaromatic ring system optionally substituted with one or more substituents selected from: halogen, C₁–C₁₀ hydrocarbyl, —O(C₁–C₁₀ hydrocarbyl), —S(C₁–C₁₀ hydrocarbyl), —SO(C₁–C₁₀ hydrocarbyl) or —SO₂ (C₁–C₁₀ hydrocarbyl), cyano, nitro, SCN, SiR₃ᶜ, COR⁷, CR⁷NOR⁸, NHOH, ONR⁷R⁸, SF₅, COOR⁷, SO₂NR⁷R⁸, OR⁹ and NR¹⁰R¹¹; and in which any ring nitrogen atom may be quaternised or oxidised;

or any two substituents of the group A may combine to form a fused 5- or 6-membered saturated or partially saturated carbocyclic or heterocyclic ring in which any carbon or quaternised nitrogen atom may be substituted with any of the substituents mentioned above for A or in which a ring carbon atom may be oxidised;

$R^6$ is hydrogen, OH, CHO, NR¹⁶R¹⁷ or C₁–C₁₀ hydrocarbyl, —O(C₁–C₁₀ hydrocarbyl), either of which may be substituted with up to two substituents chosen from OR¹⁶, COR¹⁶, COOR¹⁶, OCOR¹⁶, CN, halogen, S(O)ₚR¹⁶NR¹⁶R¹⁷, NO₂, NR¹⁶COR¹⁷, NR¹⁶CONR¹⁷R¹⁸, CONR¹⁶R¹⁷ or heterocyclyl;

$R^{16}$, $R^{17}$ and $R^{18}$ are each, independently, hydrogen, C₁–C₆ hydrocarbyl or C₁–C₆ halohydrocarbyl;

p is 0, 1 or 2; or $R^6$ and $R^7$ may together form a bridge represented by the formula —Q¹—Q²— or —Q¹—Q²—Q³—, where Q¹, Q² and Q³ each independently represent CR¹²R¹³, =CR¹², CO, NR¹⁴, =N, O or S;

$R^7$ and $R^8$ are each independently hydrogen or C₁–C₁₀ hydrocarbyl;

$R^9$ is hydrogen, C₁–C₁₀ hydrocarbyl, SO₂(C₁–C₁₀ hydrocarbyl), CHO, CO(C₁–C₁₀ hydrocarbyl), COO (C₁–C₁₀ hydrocarbyl) or CONR⁷R⁸;

$R^{10}$ and $R^{11}$ are each independently hydrogen, C₁–C₁₀ hydrocarbyl, O(C₁–C₁₀ hydrocarbyl), SO₂(C₁–C₁₀ hydrocarbyl), CHO, CO(C₁–C₁₀ hydrocarbyl), COO (C₁–C₁₀ hydrocarbyl) or CONR⁷R⁸;

any of the hydrocarbyl groups within the group A may optionally be substituted with halogen, hydroxy, SO₂NRᵃRᵇ, cyano, nitro, amino, mono- or dialkylamino, acylamino, C₁–C₆ alkoxy, C₁–C₆ haloalkoxy, C₁–C₆ alkylthio, C₁–C₆ alkylsulphinyl, C₁–C₆ alkylsulphonyl, carboxy, carboxyamide in which the groups attached to the N atom may be hydrogen or lower hydrocarbyl optionally substituted with halogen, alkoxy carbonyl or aryl and $R^{25}$ is a leaving group;

is prepared by reacting a compound of one of the following formulae:

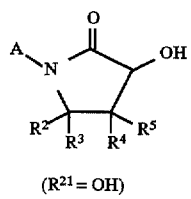

(R²¹ = OH)

II

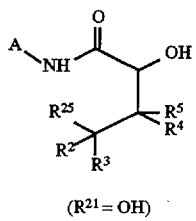

(R²¹ = OH)

III

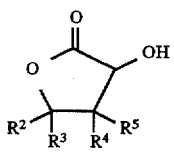

VI

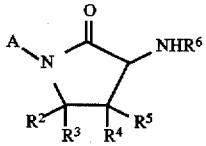

XIV

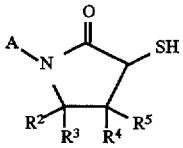

XV wherein $R^1$, $R^2$, $R^3$, $R^4$, $R^5$, $R^6$ and $R^{25}$ are as defined above; respectively with an isocyanate of formula VII:

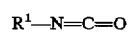

R¹—N=C=O      VII in the presence of an acid.

11. A process as claimed in claim 10, wherein the acid is a Lewis acid.

12. A process as claimed in claim 11, wherein the Lewis acid is present in a catalytic amount.

13. A process as claimed in claim 11, wherein the Lewis acid is boron trifluoride etherate.

14. A process as claimed in claim 2, wherein the strong base is an alkali metal hydride, alkoxide or hydroxide.

15. A process as claimed in claim 1, wherein $R^{25}$ is a halogen atom.

16. A process as claimed in claim 3, wherein the compound of formula IV is reacted with the compound of formula V in the presence of triethylamine and in an organic solvent selected from the group consisting of diethyl ether and tetrahydrofuran.

* * * * *